US008399422B2

(12) United States Patent
Neuberg et al.

(10) Patent No.: US 8,399,422 B2
(45) Date of Patent: Mar. 19, 2013

(54) COMPOSITIONS FOR TRANSFECTION OF OLIGONUCLEOTIDES ACTIVE FOR GENE SILENCING AND THEIR BIOLOGICAL AND THERAPEUTICAL APPLICATIONS

(75) Inventors: Patrick Neuberg, Illkirch (FR); Anne-Laure Bolcato Bellemin, Strasbourg (FR); Jean-Paul Behr, Strasbourg (FR); Patrick Erbacher, Benfeld (FR)

(73) Assignee: Polyplus-Transfection, Illkirch Cedex (FR)

( * ) Notice: Subject to any disclaimer, the term of this patent is extended or adjusted under 35 U.S.C. 154(b) by 719 days.

(21) Appl. No.: 12/226,027

(22) PCT Filed: Apr. 5, 2007

(86) PCT No.: PCT/IB2007/001774
§ 371 (c)(1),
(2), (4) Date: Nov. 5, 2009

(87) PCT Pub. No.: WO2008/004058
PCT Pub. Date: Jan. 10, 2008

(65) Prior Publication Data
US 2010/0048672 A1    Feb. 25, 2010

Related U.S. Application Data

(60) Provisional application No. 60/789,575, filed on Apr. 6, 2006.

(30) Foreign Application Priority Data

Apr. 6, 2006  (EP) .................................... 06290563

(51) Int. Cl.
*A61K 48/00*    (2006.01)
(52) U.S. Cl. ................... 514/44 R; 435/320.1; 435/325; 435/455

(58) Field of Classification Search ........................ None
See application file for complete search history.

(56) References Cited

U.S. PATENT DOCUMENTS

| 6,071,890 A   | * | 6/2000 | Scheule et al. ............... 514/44 R |
| 2004/0019008 A1 | * | 1/2004 | Lewis et al. ...................... 514/44 |
| 2006/0002991 A1 |   | 1/2006 | Essler et al. |

FOREIGN PATENT DOCUMENTS

JP    2004137143    *    5/2004

OTHER PUBLICATIONS

Ilies et al, "Pyridinium cationic lipids in gene delivery: an in vitro and in vivo comparison of transfection efficiency versus a tetraalkylammonium congener", Archives of Biochemistry and Biophysics 435 (2005); 217-226.

Quek et al, "Synthesis and properties of N,N'-dialkylimidazolium bis(nonafluorobutane-1-sulfonyl)imides: a new subfamily of ionic liquids", Tetrahedron 62 (2006) 3137-3145.

* cited by examiner

*Primary Examiner* — Jennifer Pitrak McDonald
(74) *Attorney, Agent, or Firm* — Nixon & Vanderhye P.C.

(57) ABSTRACT

The invention relates to compositions of transfection comprising an oligonucleotide and an amphiphilic cationic molecule of formula (I) wherein, —X is N—$R_1$, S or O, $R_1$ being a C1-C4 alkyl radical or an hydroxylated C3-C6 alkyl radical, $R_2$ and $R_3$, identical or different, represent H or a C1-C4 alkyl radical, or $R_2$ and $R_3$ are linked together to form a saturated or unsaturated cycle or a heterocycle having 5 or 6 elements, E is a C1-C5 alkyl spacer, $R_4$ and $R_5$, identical or different, represent saturated or unsaturated, linear or branched, C10-C36 hydrocarbon or fluorocarbon chains, optionally comprising C3-C6 cycloalkyl, A– is a biocompatible anion. The invention relates to compositions active for oligonucleotides delivery into eukaryotic cells in culture, ex vivo or in vivo. The invention relates to compositions of transfection comprising an oligonucleotide active for RNA interference. Such compositions can be used as tools for biological studies or as drugs for therapies.

24 Claims, 6 Drawing Sheets

Figure 1:
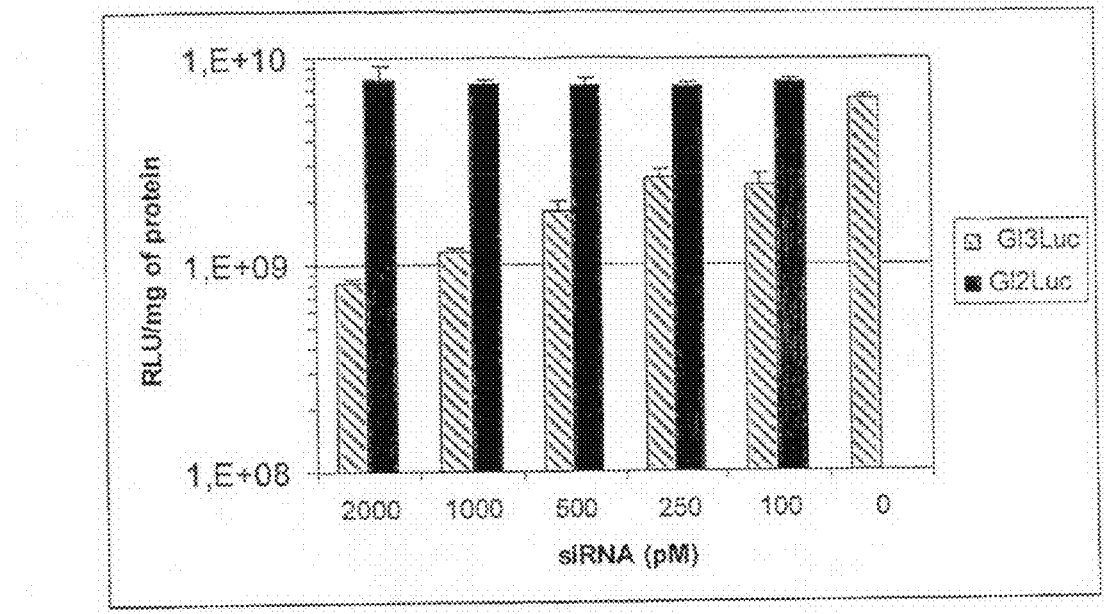

COMPOSITIONS FOR TRANSFECTION OF OLIGONUCLEOTIDES ACTIVE FOR GENE SILENCING AND THEIR BIOLOGICAL AND THERAPEUTICAL APPLICATIONS

This application is the U.S. national phase of International Application No. PCT/IB2007/001774, filed 5 Apr. 2007, which designated the U.S. and claims the benefit of European Patent Application No. 06290563.3 filed 6 Apr. 2006 and U.S. Provisional Application No. 60/789,575 filed 6 Apr. 2006, the entire contents of each of which are hereby incorporated by reference.

The invention relates to means, compositions and methods, for delivery of oligonucleotides, particularly small interfering RNA (designated as siRNA thereafter) leading to RNA interference (RNAi), to eukaryotic cells in culture, ex vivo or in vivo.

RNA interference (RNAi) is a potent technology for gene silencing at the mRNA level (Fire, 1999) (Tuschl et al., 1999), providing sequence-specific mRNA degradation and inhibition of protein production (Yang et al., 2000) (Zamore et al., 2000) (Hammond et al., 2000) (Parrish et al., 2000). RNAi is a highly effective biochemical process due to a predictable design of active sequences of short dsRNA and to the targeting of specific mRNA. When introduced in the cytoplasm of cells by transfection with a delivery vector, siRNA has been shown to effectively silence exogenous or endogenous genes in a variety of mammalian cells (Elbashir et al., 2001).

Small interfering RNAs are short double-stranded RNAs (dsRNAs) having a length preferably ranging from 19 to 29 nucleotides (see patents WO 0244321, WO 01/075164 A3, EP20010985833, and references (Siolas et al., 2005) (Kim et al., 2005)), particularly 19-23 nucleotides, and have RNAi activity in mammalian cell culture systems (Parrish et al., 2000) (Elbashir et al., 2001) (Tuschl, 2001). Short dsRNAs, when base-paired, with unpaired 3' overhanging ends, act as the guide for sequence-specific mRNA degradation. The most effective short dsRNAs were composed of two 21 nucleotide long strands which were paired such that 1-3, particularly 2, nucleotides 3'-overhangs are present on both ends of the dsRNA (Elbashir et al., 2001).

The success of RNAi depends both on dsRNA length, sequence and chemical structure and on cellular delivery system. When compared to antisense or ribozyme technology, the secondary structure of the target mRNA is not a strong limiting factor for gene expression inhibition with siRNA. Many siRNA sequences may be effective for a given mRNA target. Thus, the stability and bioavailability of siRNA duplexes as well as the amount of dsRNA delivered to cells, and particularly in the cytoplasm, remain the limiting factors for efficient silencing rather than target accessibility by the siRNA.

Many systems of delivery are useful for introducing oligonucleotides into cells. Currently, non-viral vectors based on cationic lipid-mediated transfection, such as Oligofectamin, TRANSIT-TKO, LipofectAmine-2000, SiGuide, RNAiFect, HiperFect, or jetSi, are marketed for siRNAs delivery. In contrast to cationic polymer-based systems, cationic lipids were shown to release the nucleic acid in the cytoplasm following early endosomal rupture and complex formation with phosphatidylserine (Zelphati and Szoka, 1996).

The non viral vector system advantageously comprises cationic lipid- or polymer- or peptide-based delivery reagents. The non-viral vector system is a formulation comprising at least a delivery reagent and additional components for stabilizing the formulation, targeting cells, tissues or organs, or increasing transfection efficiency.

The present invention describes a new class of non viral transfection agents, belonging to the cationic lipids group, which are particularly adapted for the transfection of small sized oligonucleotides. Especially the specific interaction of small molecules with oligonucleotides prompted us to design a new class of transfection agents.

Many molecules bind to double stranded oligonucleotides (dsON). They can be divided into three classes with respect to their binding modes:

1) intercalation between stacked base pairs as exemplified by quinacrine or ethidium bromide;

2) electrostatic and H-bond interactions with heteroatoms from the oligonucleotide backbone as observed for the polyamines spermine or spermidine, 3) Minor Groove Binders (MGBs): extended heterocyclic structures that fill the deep minor groove of DNA and interact mainly by Van der Waals and H-bond interactions. Such oligo-heterocyclic molecules are best exemplified by the antibiotic netropsin (N-methylpyrrole-containing oligopeptide) and its analogue distamicin A (Cho and Rando, 2000).

Ribonucleotide helices show some distinct features: while intercalation remains possible, Van der Waals and electrostatic binding modes occur preferentially in the deep and sometimes shallow major groove.

In particular, tri-imidazole binders such as AR-1-144, designed as imidazole containing analogues of netropsine (Yang et al., 1999), have attracted our attention. Here the guanine N2 amino group forms a bifurcated hydrogen bond to a side-by-side Im/Im pair (Yang et al., 1999). The rest of the molecule seems to have more hydrophobic interactions within the minor groove, as shown by the parent molecule distamycin A (Yang et al., 1999).

The bisbenzimidazole dye Hoechst33258 is an equally known Minor Groove Binder and shows selectivity for AT-rich sequences of DNA. It also binds to RNA at "bulge" regions, where it fits into a pocket formed by successive base pairs, as in TAR RNA (Dassonneville et al., 1997).

The inventors have found that transfection efficiency could be obtained by combining an oligonucleotide of interest with specific amphiphilic cationic molecules stably formulated as small sized liposomes with neutral co-lipids.

It is then an object of the invention to provide new molecules useful as transfection agents.

It is another object of the invention to provide compositions of these molecules useful for transfection.

It is another object to provide a synthetic pathway and efficient purification method for said amphiphilic molecules.

According to still another object, the invention relates to a method for transfecting cells in culture and in vivo.

The invention also relates to compositions for use as pharmaceutical compositions for inducing a regulating effect on the expression of one or more target proteins responsible for or involved in genetic diseases.

It also relates to a method of treatment of patients suffering from such pathologies.

According to the invention, the new molecules useful as agents for transfection compositions of oligonucleotides, more particularly, for RNA interference, comprise a cationic moiety able to bind oligonucleotides bound to a lipophilic moiety which enables the molecule to cross the lipid bilayer of cell membranes.

The invention thus relates to amphiphilic cationic molecule of formula (I)

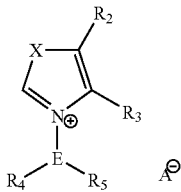

wherein:
- X is N—$R_1$, S or O, $R_1$ being a C1-C4 alkyl radical or an hydroxylated C3-C6 alkyl radical,
- $R_2$ and $R_3$, identical or different, represent H or a C1-C4 alkyl radical, or $R_2$ and $R_3$ are linked together to form a saturated or unsaturated cycle or an heterocycle having 5 or 6 elements,
- E is a C1-C5 alkyl spacer,
- $R_4$ and $R_5$, identical or different, represent saturated or unsaturated, linear or branched, C10-C36 hydrocarbon or fluorocarbon chains, said chains optionally comprising C3-C6 cycloalkyl,
- $A^-$ is a biocompatible anion.

The heterocycles formed when $R_2$ and $R_3$ are linked together are unsaturated or saturated and have 5 or 6 elements and comprise C and N, S or O as heteroatoms.

According to a preferred embodiment of the invention, $R_4$ and $R_5$ in formula (I) are C14-C36 hydrocarbon radicals and E is a C1-C4 alkyl spacer.

In a preferred group, $R_4$ and $R_5$ are identical.

In advantageous molecules, $R_4$ and $R_5$ are C18 alkyl radical and E is C1 alkyl.

In other advantageous molecules, $R_4$ and $R_5$ are C16 alkyl radicals and E is C4 alkyl.

In another preferred group, $R_4$ and $R_5$ are different.

In molecules of interest, $R_4$ and $R_5$ are C18 and C17 alkyl radicals, respectively and E is C2 alkyl.

In other molecules of interest, $R_4$ and $R_5$ are C32 and C18 alkyl radicals, respectively, and E is C1 alkyl.

Preferably, in the above groups, $R_2$ and $R_3$ are H or form together an aromatic cycle, particularly a benzo group, or an heterocycle such as a pyridyl or pyrazinyl group.

In particular, X is N—$R_1$, $R_1$ being for example a methyl radical.

Alternatively, X is S or O.

Advantageously, the counterion $A^-$ is $Cl^-$ or $OH^-$.

The invention also relates to compositions for the transfection of oligonucleotides active for gene silencing. According to an embodiment, the invention relates to compositions wherein the above defined amphiphilic molecules are formulated with neutral co-lipids that are stable upon prolonged storage.

Suitable co-lipids are phosphatidyl-ethanolamines, such as dioleoylphosphatidyl-ethanolamine (DOPE), lipid-PEG conjugate or cholesterol.

In another embodiment, the invention relates to amphiphilic molecules active without addition of co-lipids, in particular those with branched $R_4$ or $R_5$.

The invention more particularly relates to transfection compositions comprising, in addition to an amphiphile part formulated with a neutral lipid, at least one oligonucleotide responsible for the desired biological effect.

The invention thus provides a non viral delivery system suitable for introducing dsONs (ds=double strand; ON=oligonucleotide) in live cells, especially siRNAs.

Said oligonucleotides or siRNA, respectively, can be stabilized against degradation with suitable groups, selected in the group comprising purine nucleotides, pyrimidine nucleotides substituted by modified analogs such as deoxynucleotides, and/or modified nucleotide analogs such as sugar- or backbone modified ribonucleotides or deoxyribonucleotides. The oligonucleotides sequences can contain deoxyribonucleotides, ribonucleotides or nucleotide analogs (Verma and Eckstein, 1998), such as methylphosphonate (Miller, 1991), morpholino phosphorodiamidate, phosphorothioate (Zon and Geiser, 1991), PNA (Jepsen and Wengel, 2004), LNA, 2'alkyl nucleotide analogs (Kurreck, 2003).

The invention also relates to a method for obtaining the molecules of formula (I), comprising a purification and a conversion step to salt derivatives of the amphiphiles of formula (I) under a neutral form, by selective precipitation in methanol/water/acid out of the reaction medium.

Advantageously, the method of synthesis of the molecules of formula (I) comprises:

Elaboration of a branched long chain, whose hydrocarbon part is obtained by classical C—C coupling methods such as illustrated by the Grignard coupling reaction to esters or aldehydes. The synthesized hydrophobic part contains a primary or secondary alcohol as illustrated in formula IV:

HO-E-R4(R5)        (IV)

Activation of the alcohol functionality by conversion to a methanesulfonyl derivative, of formula (V) MsO-E-R4(R5) and/or other classical activated derivatives such as halogeno derivatives;

reacting said activated derivatives, in particular methanesulfonyl derivatives, with an heterocycle of formula (VI)

wherein X is N—R1, S or O under specified conditions to obtain (I)

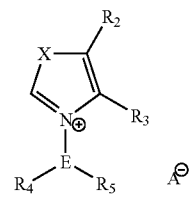

or reacting said methanesulfonyl derivative (V) with an heterocycle illustrated in formula (VII)

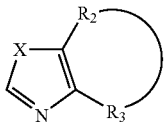
(VII)

under specified conditions to obtain the heterocycle of formula (VIII)

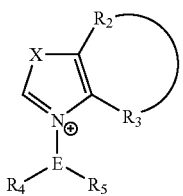
(VIII)

In said formulae, the substituents are as above defined with respect to formula (I).

When X represents —N—$R_1$, said method further comprises an alkylation step for X, for example the methylation of N with methyliodide.

The alcohol HO-E-$R_4$($R_5$) (IV) is activated by conversion to its methanesulfonyl ester. A suspension of the alcohol in a solvent like pyridine is advantageously prepared, a high concentration being used for the reaction with methanesulfonyl chloride.

The addition of the heterocycle to the sulfonate derivative Ms-O-E-R4(R5) is preferably carried out by heating the reaction mixture at a temperature of about 50-100° C., advantageously about 80° C.

Purification of the described amphiphilic molecules out of the reaction mixture, and conversion into a biocompatible salt form, are advantageously carried out by a specific precipitation method. Such a precipitation consists in a dilution in a methanol plus water mixture followed by controlled acidification by an acid HA generating a precipitate of the corresponding A– salt (I).

The precipitation can also be done with other alcohol/water mixtures, such as isopropanol/water mixtures, that are acidified with aqueous acids, in order to get the corresponding salts, such as chlorhydrate salts by acidification with chlorohydric acid.

The liposomes are prepared by dissolving in an organic solvent the co-lipid and derivative of formula (I) and injection of this solution into water.

An appropriate organic solvent is ethanol. The resulting liposomal formulations in water advantageously have a size of about 110 nm with a narrow distribution in their size.

Appropriate siRNA or oligonucleotide are then complexed with said liposome formulation.

As shown in the examples, the molecules of the invention are particularly efficient systems for delivering oligonucleotides, especially siRNA, to eukaryotic cells in culture.

The invention thus also relates to a method for transfection of cells by oligonucleotides mediating gene silencing, particularly siRNA inducing RNAi, comprising introduction of a composition such as above defined in the cells.

Said compositions provide selective and high endogenous gene silencing efficiency over many days at very low siRNA concentration, particularly at nanomolar and down to picomolar siRNA concentrations. The high gene silencing thus obtained is exemplified by many targets, such as luciferase, human GAPDH, human lamin A/C, or murine vimentin genes, without side effects or off-target effects, or cell toxicity.

Said method can be used with eukaryotic cells in culture (both adherent or non adherent cells), for functional genomic, target validation or in vivo or ex vivo therapeutic applications.

The method of the invention can be performed in the presence of serum using the transfection protocols.

The method of the invention is particularly useful to mediate gene silencing or HTS applications of siRNA or oligonucleotide when a reverse transfection procedure is performed.

Advantageously, the above defined compositions are able to induce a regulating effect on the expression of one or more target proteins responsible for or involved in genetic diseases.

The invention thus also relates to transfection compositions such as above defined for use as drugs.

Said compositions are advantageously under a form suitable for an administration by the oral, systemic, or topical route and may be in association with a pharmaceutically acceptable inert carrier.

Said compositions are particularly useful for the treatment of cancer, viral infections, or parasites infections.

Others characteristics and advantages of the invention will be given in the following examples, with references to FIGS. 1 to 10, which represent, respectively:

FIG. 1: Selective and efficient RNA interference of luciferase gene (pGL3) stably expressed by A549-GL3Luc cells by GL3Luc siRNA transfected with the formulation MONI/DOPE (1 mM/1 mM in ethanol).

A549-GL3Luc cells, stably expressing the luciferase gene, were transfected (in 24-well tissue culture plate format) with GL3Luc siRNA, concentration ranging from 100 to 2000 pM, complexed with 2 µl of equimolar formulation composed of MONI/DOPE (1 mM/1 mM in Ethanol). As unspecific siRNA control, siRNA matching the GL2 luciferase sequence were transfected in the same conditions. Luciferase gene expression was measured after 48 h incubation period. Experiments were made in triplicates and the luciferase activity was expressed as Relative Light Unit (RLU) normalized by the content of protein in the cell lysates (mg of protein).

Figure 2:
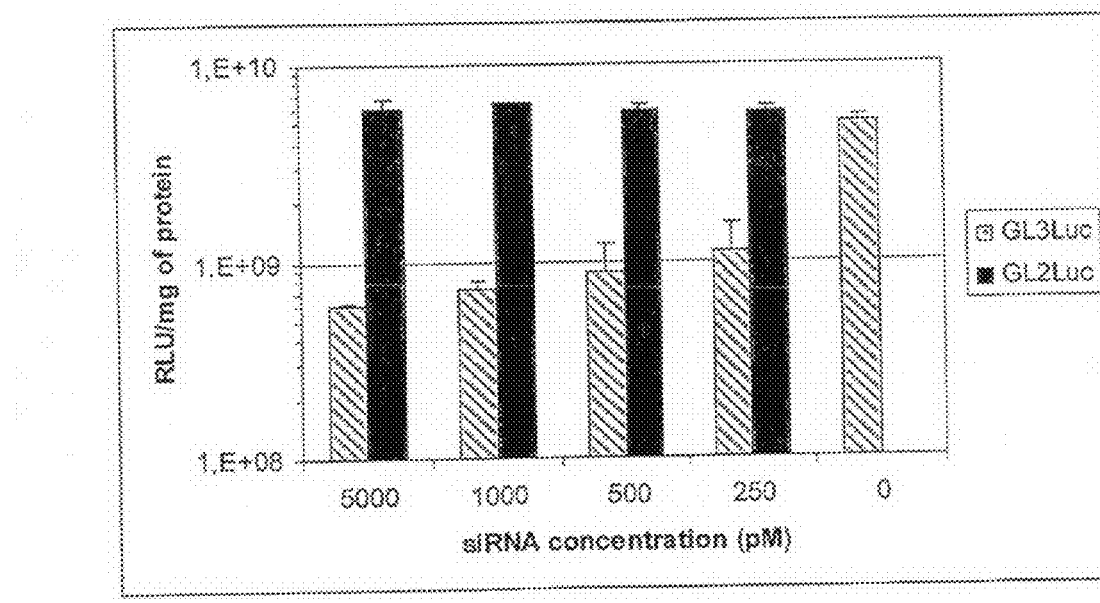

FIG. 2: Selective and efficient RNA interference of luciferase gene (pGL3) stably expressed by A549-GL3Luc cells by GL3Luc siRNA transfected with the formulation MONBI/DOPE (1 mM/2 mM in ethanol).

A549-GL3Luc cells, stably expressing the luciferase gene, were transfected (in 24-well tissue culture plate format) with GL3Luc siRNA, concentration ranging from 250 to 5000 pM, complexed with 2 µl of formulation composed of MONBI/DOPE (1 mM/2 mM in Ethanol). As unspecific siRNA control, siRNA matching the GL2 luciferase sequence were transfected in the same conditions. Luciferase gene expression was measured after 48 h incubation period. Experiments were made in triplicates and the luciferase activity was expressed as Relative Light Unit (RLU) normalized by the content of protein in the cell lysates (mg of protein).

Figure 3:
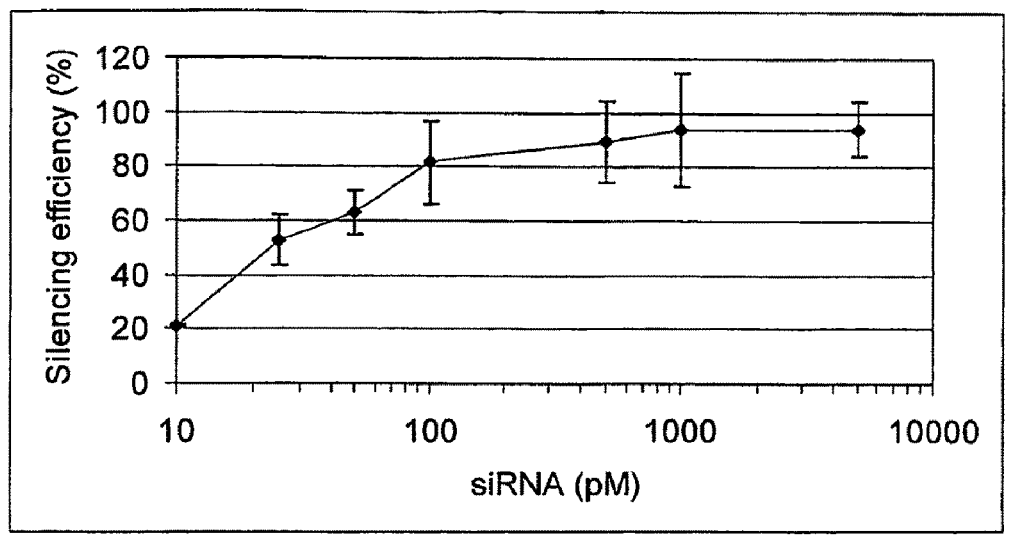

FIG. 3: Silencing of luciferase gene (pGL3) by GL3Luc siRNA transfected with the formulation MONI/DOPE (1 mM/1 mM in ethanol), effective even at the picomolar range of siRNA.

A549-GL3Luc cells, stably expressing the luciferase gene, were transfected (24-well plate) with GL3Luc siRNA complexed with the equimolar formulation composed of MONI/DOPE (1 mM/1 mM in Ethanol) with a siRNA concentration ranging from 10 to 5000 pM. Luciferase gene expression was measured after 48 h incubation period. Experiments were made in triplicates and the GL3 luciferase silencing efficiency was calculated from the endogenous luciferase level of untransfected A549-GL3Luc cells normalized by the content of protein in the cell lysates.

Figure 4:
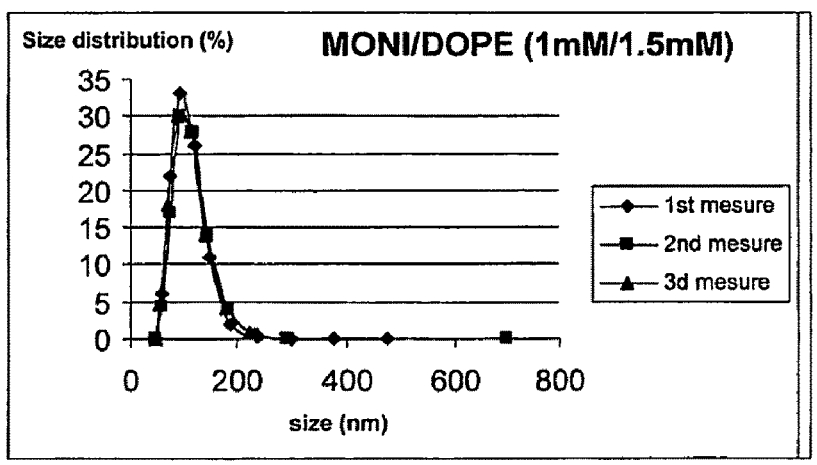

FIG. 4: DLS measurements of particles size showing a relatively monodisperse population of liposomes with sizes of 100+/−10 nm.

Liposomal preparations at 1 mmole of amphiphile with varying concentrations of DOPE were prepared in milliQ water, as described above. The particle size of these liposomal preparations was determined by light scattering using a Zetamaster (Malvern Instrument, Orsay, France) with the following specifications: sampling time, 30 s; 3 measurements per sample; medium viscosity, 1.0 cP; refractive index (RI) medium, 1.335; RI particle, 1.47; temperature: 25° C., at 633 nm laser wavelength. Particles size determination presented in the figure was obtained from the liposomal preparation at 1 mM MONI and 1.5 mM DOPE in water (stability of liposomes after 1 month of storage at 5° C.). Measurements were made in triplicates.

Figure 5:
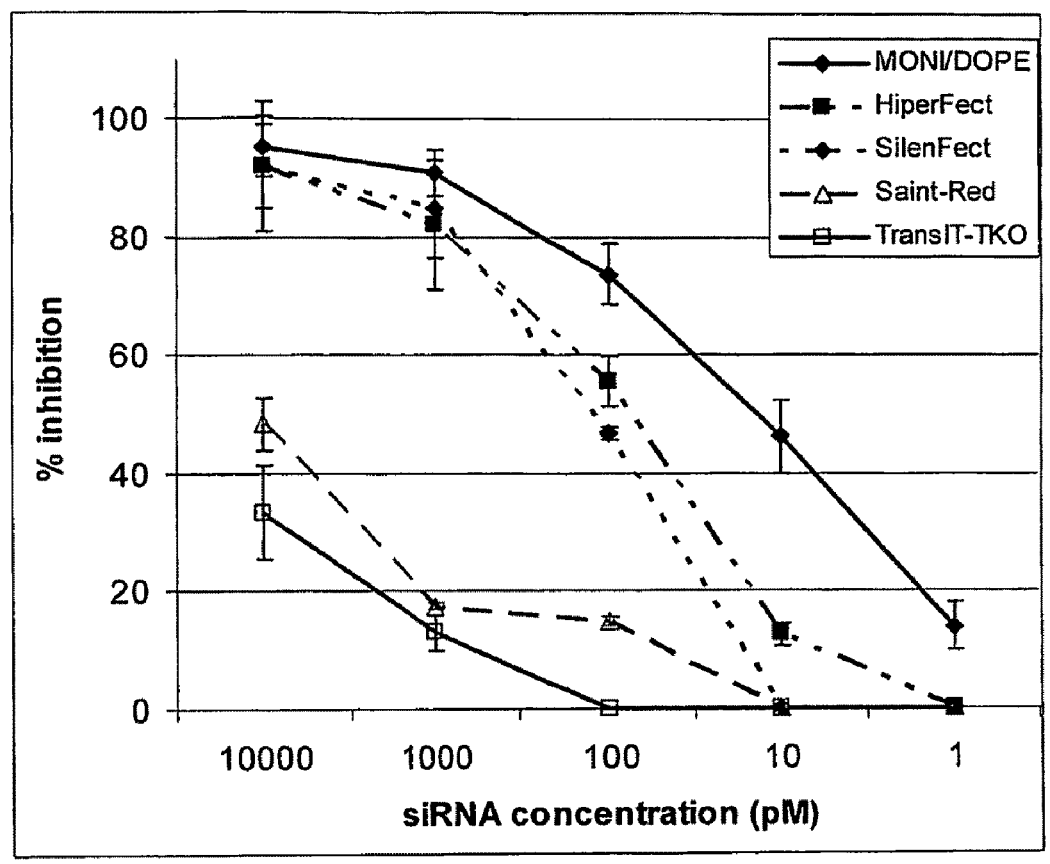

FIG. 5: Comparative silencing efficiency of luciferase gene (pGL3) by GL3Luc siRNA transfected with the formulation MONI/DOPE (1 mM/2 mM) in water and many commercially available siRNA transfection reagents.

A549-GL3Luc cells, stably expressing the luciferase gene, were transfected (24-well plate) with GL3Luc siRNA complexed with 2 µl of liposomal formulation composed of MONI/DOPE in Ethanol (1 mM/2 mM) in water and many commercially available transfection reagents with a siRNA concentration ranging from 1 to 10,000 pM. Commercial transfection reagents were used at their optimal conditions following the recommendations of manufacturers (see Material and methods). Luciferase gene expression was measured after 48 h incubation period. Experiments were made in triplicates and the GL3 luciferase silencing efficiency was calculated from the endogenous luciferase level of non-transfected A549-GL3Luc cells normalized by the content of protein in the cell lysates.

Figure 6:
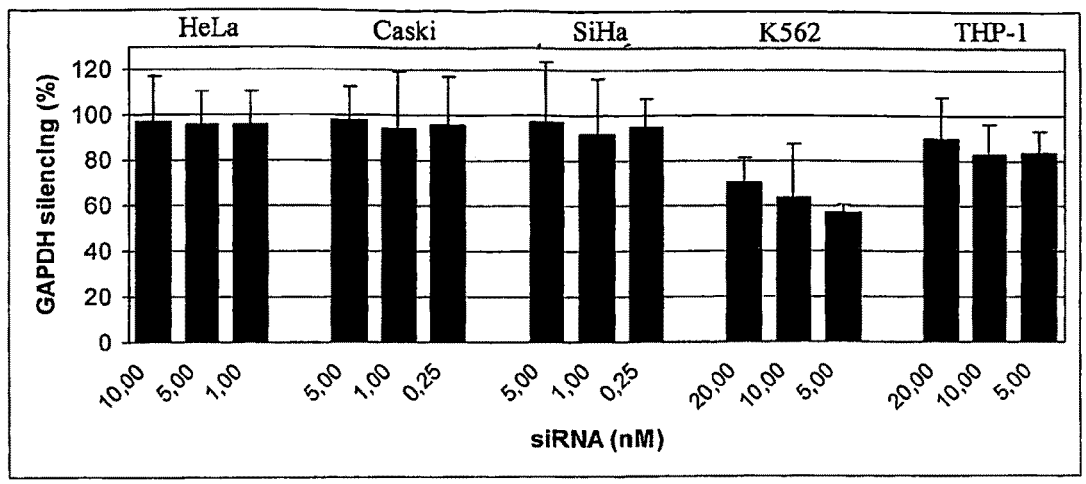

FIG. 6: Efficient GAPDH gene silencing in different cell lines after siRNA transfection with the formulation of MONI/DOPE in water (1 mM/2 mM).

Adherent HeLa, Caski, and SIHA cells and non-adherent K562 and THP-1 cells were transfected with GAPDH siRNA complexed with the formulation MONI/DOPE (1 mM/2 mM) in water. GAPDH mRNA level was measured by branched DNA assay after 48 h incubation period. As unspecific control, siRNA matching an unrelated sequence (lamin A/C) was transfected in the same conditions. Experiments were made in triplicates and the GAPDH silencing efficiency was calculated from the endogenously GAPDH level of non-transfected cells.

Figure 7:
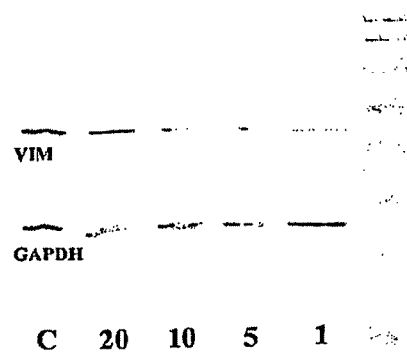

FIG. 7: The MONI/DOPE formulation mediates efficient Vimentin gene silencing in 3T3 cells.

3T3 cells were transfected with vimentin siRNA complexed with the MONI/DOPE formulation with a siRNA concentration ranging from 20 nM to 1 nM. Vimentin protein level was determined by Western blot after 48 h incubation period. As control of protein level in cell lysates, GAPDH protein was also detected.

Figure 8:
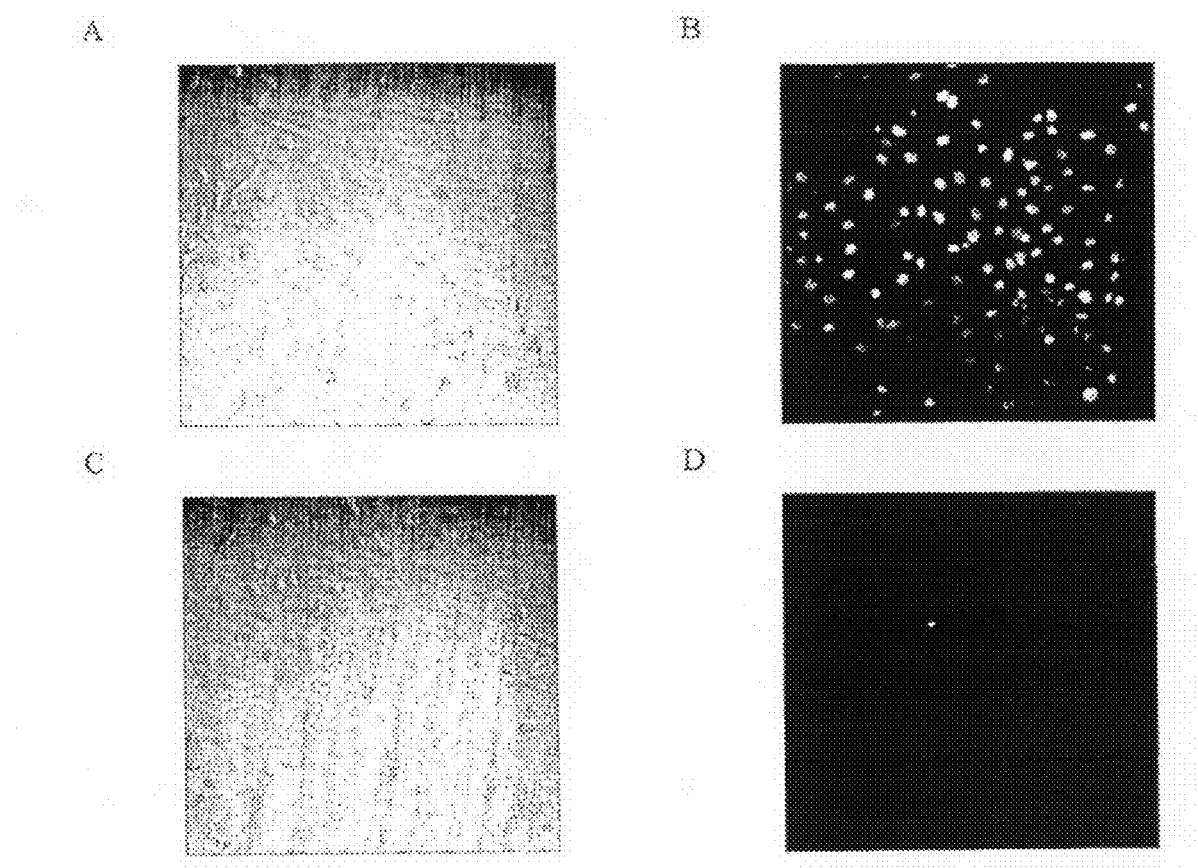

FIG. 8: The liposomal MONI/DOPE formulation mediates efficient Lamin A/C gene silencing in HeLa cells.

HeLa cells were transfected in medium containing serum (in 24-well plate) with Lamin A/C siRNA (5 nM) complexed with 2 µl of liposomal formulation composed of MONI/DOPE in Ethanol (1 mM/2 mM) in water. The lamin A/C protein was detected by immunofluorescence staining 48 h post-transfection and observed by microscopy (C and D) and compared to non transfected cells (A and B).

Figure 9:
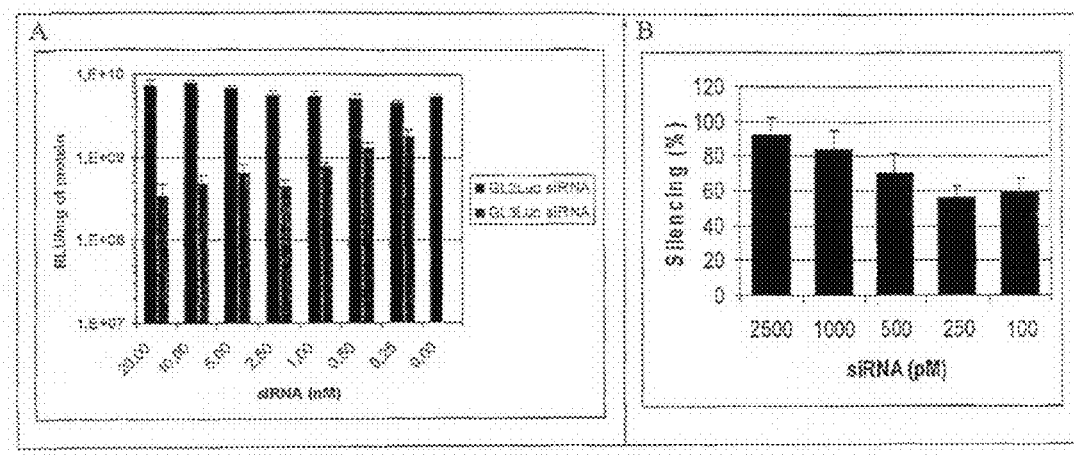

FIG. 9: Reverse transfection of siRNA complexed with the formulation MONI/DOPE in water (1 mM/2 mM) induces selective and highly efficient gene silencing.

GL3Luc siRNA diluted in 50 µl of serum free medium were complexed (in 96-well tissue culture plate format, n=6) for 5 minutes with 1 µl of formulation composed of MONI/DOPE in water (1 mM/2 mM). Then, 10,000 A549-GL3Luc cells, stably expressing the luciferase gene, in 125 µl of medium containing serum were added per well. Luciferase gene expression was measured after 48 h incubation period. As unspecific siRNA control, siRNA matching the GL2 luciferase sequence were transfected in the same conditions. Luciferase gene expression was measured after 48 h incubation period and the luciferase activity was expressed as Relative Light Unit (RLU) normalized by the content of protein in the cell lysates (mg of protein). GL3 luciferase silencing efficiency (FIG. 3B) was calculated from the endogenous luciferase level of untransfected A549-GL3Luc cells normalized by the content of protein in the cell lysates.

Figure 10:
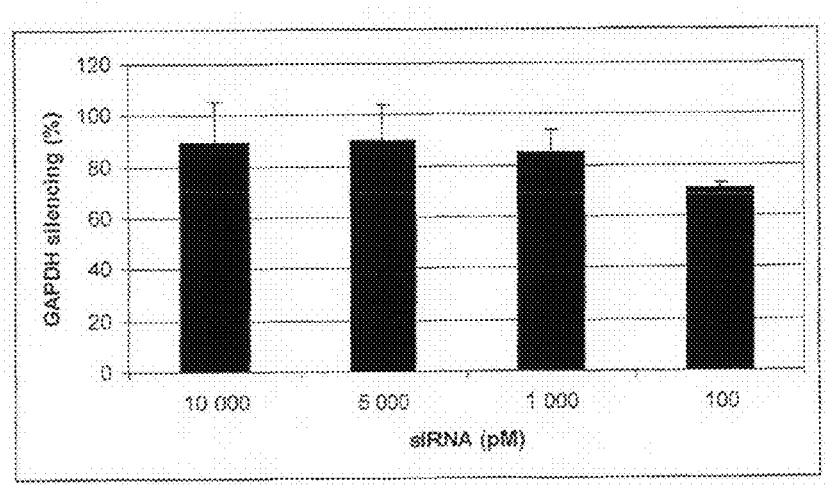

FIG. 10: Reverse transfection of siRNA complexed with the formulation MONI/DOPE in water (1 mM/2 mM) was efficient to silence the endogenous GAPDH of MCF-7 cells.

The optimized reverse procedure of siRNA transfection was applied to silence the GAPDH gene of MCF-7 cells using siRNA concentration range of 100 pM to 10 nM and 1 µl of the liposomal MONI/DOPE formulation. GAPDH mRNA level was measured by QuantiGene® Branched DNA Assay 48 h post-transfection. As unspecific control, siRNA matching an unrelated sequence (lamin A/C) was transfected in the same conditions. GAPDH silencing efficiency was calculated from the endogenously GAPDH level of non-transfected cells (n=6 per condition).

MATERIALS AND METHODS

Chemicals and Oligonucleotides

Oligonucleotides were chemically synthesised and PAGE purified by Eurogentec (Belgium). Oligonucleotides were annealed in 1× Annealing buffer (50 mM KAcetate, 50 mM MgAcetate) (Eurogentec) for 2 min. at 95° C., followed by 2-4 hours incubation at room temperature. HiperFect and SilentFect reagents were from Qiagen and BioRad, respectively (United States). TransIT-TKO and Saint-Red reagents were from Mirus Corporation and Synvolux, respectively. GAPDH SMART Pool® reagent was from Dharmacon.

SiRNA Duplexes Used:

```
GL3Luc siRNA duplex          5'-CUUACGCUGAGUACUUCGA(dT)2-3'
(SEQ ID N° 1 and SEQ ID N° 2)   3'-(dT)2GAAUGCGACUCAUGAAGCU-5'

GL2Luc siRNA duplex          5'-CGUACGCGGAAUACUUCGA(dT)2-3'
(SEQ ID N° 3 and SEQ ID N° 4)   3'-(dT)2GCAUGCGCCUUAUGAAGCU-5'
```

-continued

```
Vimentin siRNA duplex        5'-GAAUGGUACAAAUCCAAGdTdT-3'
(SEQ ID N° 5 and SEQ ID N° 6)  3'-dTdTCUUACCAUGUUUAGGUUC-5'

Lamin A/C siRNA duplex       5'-CUGGACUUCCAGAAGAACAdTdT-3'
(SEQ ID N° 7 and SEQ ID N° 8)  3'-dTdTGACCUGAAGGUCUUCUUGU-5'
```

All reagents for chemistry and starting material were purchased from Sigma-Aldrich (France) and were used without prior purification. Solvents were ordered from SDS-Carlo Erba (France). Diethylether was dried and distilled over sodium benzophenone. Magnesium turnings special for Grignard reagent were purchased from Fisher Scientific (France). Dioleoylphosphatidylethanolamine (DOPE) is from Fluka (Sigma-Aldrich).

Examples 1 to 7 Relate to the Synthesis of Amphiphilic Molecules as Identified in Table 1.

TABLE 1

| Abbreviation | Chemical structure of amphiphilic molecule | Chemical Name | Aromatic Part | Spacer Group E | Lateral chains R4/R5 | R4 | R5 |
| --- | --- | --- | --- | --- | --- | --- | --- |
| MONI | (structure) | 1-Methyl-3-(1-Octadecyl-Nonadecyl)-3H-Imidazol-1-ium chloride | Methyl-3H-imidazolium | C1 | identical | C18 (linear) | C18 (linear) |
| MONBI | (structure) | 1-Methyl-3-(1-Octadecyl-Nonadecyl)-3H-Benzo-Imidazol-1-ium Chloride | Methyl-3H-benzoimidazol-1-ium | C1 | identical | C18 (linear) | C18 (linear) |
| HEIC | (structure) | 1-(2-Heptadecyl-Eicosyl)-3-methyl-3H-Imidazol-1-ium Chloride | Methyl-3H-imidazolium | C2 | different | C18 (linear) | C17 (linear) |
| HEMB | (structure) | 3-(2-Heptadecyl-Eicosyl)-1-Methyl-3H-Benzoimidazol-1-ium chloride | Methyl-3H-benzoimidazol-1-ium | C2 | different | C18 (linear) | C17 (linear) |
| HET | (structure) | 3-(2-Heptadecyl-Eicosyl)-Thiazol-3-ium chloride | Thiazol-3-ium | C2 | different | C18 (linear) | C17 (linear) |
| HEMI | (structure) | 1-(4-Hexadecyl-Eicodul)-Methyl-3H-Imidazol-1-ium chloride | Methyl-3H-imidazolium | C4 | Identical | C16 (linear) | C16 (linear) |

TABLE 1-continued

| Abbreviation | Chemical structure of amphiphilic molecule | Chemical Name | Aromatic Part | Spacer Group E | Lateral chains R4/R5 | R4 | R5 |
|---|---|---|---|---|---|---|---|
| BIA | 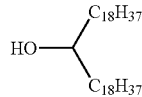 | ((Branched Imidazolium Amphiphile)) 1-methyl-3-(1-octadecyl-5-tetradecyl-nonadecyl)-3H-imidazol-1-ium chloride | Methyl-3H-imidazolium | C1 | different | C32 (branched) | C18 (linear) |

Synthesis of MONI

Synthesis of the Secondary Long-Chain Alcohol 19-hydroxyheptatriacontane S3

$C_{37}H_{76}O$; MW=537.00

Magnesium turnings (583 mg, 24 mmoles, MW=24.31) are introduced in an oven-dried two-necked reaction vessel equipped with a refrigeration column. 1-Iodooctadecane (7.608 mg, 20 mmoles, MW=380.39), previously dissolved in dry diethylether (20 ml, distilled over sodium benzophenone), is added drop-wise to the metal turnings with a syringe. During the addition the reaction is slightly heated with a fan (hairdryer), in order to maintain a constant reflux of ether. The formation of organomagnesium reagent (Grignard reagent) has started when the reaction mixture turns greyish. After the complete addition, of the iodoalkane solution, the reaction mixture is heated to maintain reflux of ether during one hour by placing the reaction vessel in an oil bath in order to drive the conversion of the iodoalkane into the corresponding Grignard reagent.

The reaction mixture is cooled to room temperature; ethyl formate (444.5 mg, 6 mmoles, MW=74.04), dissolved dry distilled diethylether (25 ml), is added drop-wise to the Grignard reagent at 20° C. The reaction warms up only slightly upon the addition. The reaction mixture is stirred for 18 hours at room temperature in order to complete the coupling reaction of this long-chain Grignard reagent onto the ester. The reaction is poured onto ice-methanol (200 g+100 ml) and acidified with concentrated chlorohydric acid to acidic pH. The resulting solid is filtered off, washed with methanol and acetone, and dried under vacuum. The solid will form an agglomerate that is washed with dichloromethane, then dissolved and recrystallized in tetrahydrofurane (THF): 1.5 g of the crude alcohol are dissolved in 250 ml of THF at 60° C. This solution, while still hot, is filtered through a filtering paper disk under vacuum. Acetone (200 ml) is added to the filtered solution in order to precipitate the final secondary alcohol, which is filtered off and washed with acetone. This purification method by precipitation in THF/acetone is applied to the total amount of crude alcohol.

In total, 3.18 g of alcohol have been prepared and purified, corresponding to 5.9 mmoles (MW=537.00). The yield of the reaction is 60% based on consumed iodoalcane (98% based on ethyl formate).

The final 19-hydroxyheptatriacontane is characterized by its $^1H$ NMR spectra confirming its purity.

Analysis of 19-Hydroxyheptatriacontane S3:

1H-NMR (nuclear magnetic resonance from proton) in $CDCl_3$:

0.90 ppm (triplet, J=7.0 Hz, 6H, terminal methyls of both chains); 1.27 ppm (large multiplet, 64H, $CH_2$ from fatty alkylchains); 1.45 ppm (broad multiplet, 4H, $CH_2$ beta position from alcohol); 1.58 ppm (broad signal from hydroxyl and from water traces); 3.60 ppm (multiplet, 1H, CH alpha position from alcohol).

Synthesis of 9-octadecyl-nonadecyl methanesulfonate S4 (=Activation of the Secondary Alcohol by Mesylation)

$C_{38}H_{78}O_3S$; MW=615.09

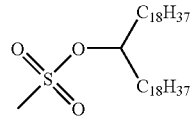

A suspension of the secondary alcohol (2.42 g, 4.5 mmoles) is prepared in 45 ml of dry pyridine in a 100 ml reaction vessel (high concentration being critical for correct conversion). 3.5 ml of methanesulfonylchloride (5.15 g, 45 mmoles) are added with a syringe into the reaction vessel in small portions. The reaction mixture does not heat notably, so the addition can be done at room temperature. The white suspension upon contact with the methanesulfonylchloride turns slightly yellow. After one hour the reaction has become more homogenous, and turns to beige colour. After 24 hours the reaction has become dark-brown coloured.

The reaction mixture is poured into 250 ml of methanol where the products, but also un-reacted alcohol, will precipitate.

This precipitate is isolated by filtration, washed with methanol and dried under vacuum. The solid is dissolved in 500 ml dichloromethane, where only the mesylated product is soluble; remaining un-reacted alcohol can be filtered off through paper.

The final 9-(octadecyl)nonadecyl methanesulfonate is obtained after complete evaporation of the dichloromethane in 69% yield (1.63 g; 2.65 mmoles: MW=615.09).

It is characterized by its $^1H$ NMR spectra.

Analysis of 9-(Octadecyl)Nonadecyl Methanesulfonate:

1H-NMR (nuclear magnetic resonance from proton) in $CDCl_3$:

0.90 ppm (triplet, J=7.0 Hz, 6H, terminal methyls of both chains); 1.27 ppm (large multiplet, 60H, CH$_2$ from fatty alkylchains); 1.40 ppm (broad multiplet inside previous signal, 4H, CH$_2$ on gamma position from mesylate); 1.69 ppm (broad multiplet, 4H, CH$_2$ on beta position from mesylate); 3.01 ppm (singlet, 3H, CH$_3$ from mesylate); 4.72 ppm (quintuplet, J=6.1 Hz, 1H, CH alpha position from mesylate).

Synthesis of 1-Methyl-3-(1-Octadecyl-Nonadecyl)-3H-Imidazol-1-ium chloride (=MONI)

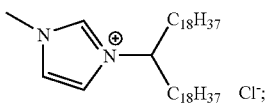

$C_{41}H_{81}ClN_2$; MW=637.55

The reaction is a direct substitution of the mesylate by the aromatic base on the secondary carbon atom. As the reaction is slow, the methylimidazole was used in large excess as a solvent.

9-(octadecyl) monadecyl methanesulfonate (1.63 g, 2.65 mmoles; MW=615.09) is introduced in a 100 ml reaction vessel topped with a refrigerating column. 80 ml of methylimidazole is added and the methanesulfonate forms a suspension. The reaction is heated at 80° C. for 6 days. The reaction mixture then turns to orange colour and becomes homogenous.

After cooling to room temperature the reaction mixture is poured in a larger flask and completed with 150 ml of methanol. This mixture is filtered through paper. The filter is washed with 80 ml of methanol. The small insoluble part is mostly un-reacted mesylate, which can be seen by NMR analysis. This filtrate is divided in three equal parts prior to purification for ease of handling.

One hundred ml of the mixture is completed with 600 ml of methanol and filtered again through paper. Then 300 ml of water were added. The mixture stays homogenous, then was acidified progressively by adding small amounts of concentrated chlorohydric acid, while controlling the pH. The addition continued was until the pH drops to 2-3. This mixture, upon standing at room temperature forms a gelatinous precipitate. To drive the precipitation, the mixture is kept at 5° C. for 18 hours. The final suspension is poured onto a paper filter and the obtained solid is washed with an alcohol mixture (700 ml methanol, 300 ml sterile water containing 1 ml concentrated chlorohydric acid) and filtered off again. The same procedure is applied to the remaining methanolic phases.

This way 517 mg of crude 3-[9-(octadecyl)nonadecyl]-1-methyl-3H-imidazolium chloride are obtained.

A control by NMR spectra shows weak contamination of this solid with methylimidazole. A second purification step is applied.

The solid is dissolved in 70 ml of methanol while stirring at 60° C. and the methanolic solution is decanted from the remaining solid. This solid residue is washed a second time with warm methanol. The insoluble part is different from product as revealed by NMR spectra. The methanolic solutions are completed with 60 ml of sterile water that has previously been acidified with 0.2 ml concentrated chlorohydric acid. This solution gels at room temperature, and is placed 18 h at 5° C. for completion of the precipitation. The gel-like solution is filtered through paper. The dry solid is re-dissolved in a mixture of equal parts of methanol and dichloromethane (250 ml) then with pure dichloromethane (250 ml). After evaporation of the solvents 481 mg of a white solid are obtained. This procedure is repeated on twice on the remaining reaction mixture (2.26 mmoles; 85% yield; MW=637.55).

NMR analysis shows absence of the previous impurities and an elemental microanalysis on this final product confirms its purity.

Analysis:

1H-NMR (Nuclear Magnetic Resonance from Proton) of MONI in CDCl$_3$:

0.90 ppm (triplet, J=6.9 Hz, 6H, terminal methyls of both chains); 1.09 ppm (multiplet; 2H at gamma' from imidazolium ring); 1.27 ppm (large multiplet, 62H, CH$_2$ from fatty alkylchains); 1.85 ppm (multiplet, 4H, CH$_2$ at beta position from imidazolium); 4.18 ppm (singlet, 3H, methyl on imidazolium ring); 7.02 ppm (singlet, 1H, C4H or C5H of imidazolium); 7.13 ppm (singlet, 1H, C5H or $\overline{C4H}$ from imidazolium); 11.17 ppm (singlet, 1H, C2$\overline{H}$ from imidazolium).

Indirect $^{13}$C-NMR (DEPT135; $\overline{D}$EPT90) in CDCl$_3$:

CH and CH$_3$ are (−); CH$_2$ are (+)

123.1 ppm (−) (C2 from imidazolium); 119.2 ppm (−) (C4 and 5 from imidazolium); 62.8 ppm (−) (methyl on N3 from imidazolium); 36.9 ppm (−) (CH on N1 from imidazolium); 35.5 ppm (+) (C from fatty chains); 31.9 ppm (+) (C from fatty chains); 29.72 ppm (+) (C from fatty chains); 29.67 ppm (+) (C from fatty chains); 29.65 ppm (+) (C from fatty chains); 29.60 ppm (+) (C from fatty chains); 29.53 ppm (+) (C from fatty chains); 29.38 ppm (+) (C from fatty chains); 29.35 ppm (+) (C from fatty chains); 29.15 ppm (+) (C from fatty chains); 25.94 ppm (+) (C from fatty chains); 22.71 (+) (C from fatty chains); 14.15 ppm (−) (CH$_3$ end-groups from fatty chains).

Infrared Absorption (IR) Spectroscopy of MONI:

Absorbance peaks are characterized by their wavelength numbers (cm$^{-1}$) and their respective absorbance, considered as strong (s), medium (m) or weak (w):

3130 (m); 3035 (s); 2955 (s); 2920 (s); 2850 (s); 1570 (s); 1560 (m); 1470 (s); 1430 (w); 1375 (w); 1160 (s); 750 (w); 725 (m).

This IR absorption profile is comparable with the reported spectrum of 1-Ethyl-3-methylimidazolium chloride, and is consistent with its chemical structure.

Example 2

Synthesis of 1-Methyl-3-(1-Octadecyl-Nonadecyl)-3H-Benzo-imidazol-1-ium chloride (MONBI)

9-(octadecyl)nonadecyl methanesulfonate (0.1 mmole) dissolved in 7 ml of methyl-ethyketone (MEK) are heated for 3 days in presence of 0.6 mmoles benzimidazole. After evaporation of the solvents the crude product is purified by silica gel chromatography applying a methanol/dichloromethane gradient. 0.015 mmoles of neutral N1 substituted benzimidazole product are isolated, which is methylated with a large excess of methyliodide in MEK while heating for 1 day. The methylation reaction is quantitative, and after purification by silica gel chromatography on a methanol/dichloromethane gradient 10 mg MONBI is obtained.

$^1$H-NMR (Nuclear Magnetic Resonance of Proton) of MONBI in CDCl$_3$:

0.89 ppm (triplet, J=6.9 Hz, 6H, terminal methyls of both chains); 1.27 ppm (large multiplet, 64H, CH$_2$ from fatty alkylchains); 2.1 ppm (large multiplet, 4H, CH$_2$ at beta position from benzimidazolium nitrogen); 4.39 ppm (singlet, 3H, methyl on N3 of benzimidazolium ring); 4.65 ppm (CH connected to benzimidazolium N1); 7.72 ppm (multiplet, 4H, benzo-ring protons); 11.37 ppm (singlet, 1H, C2H from benzimidazolium).

The reaction scheme is given herein:

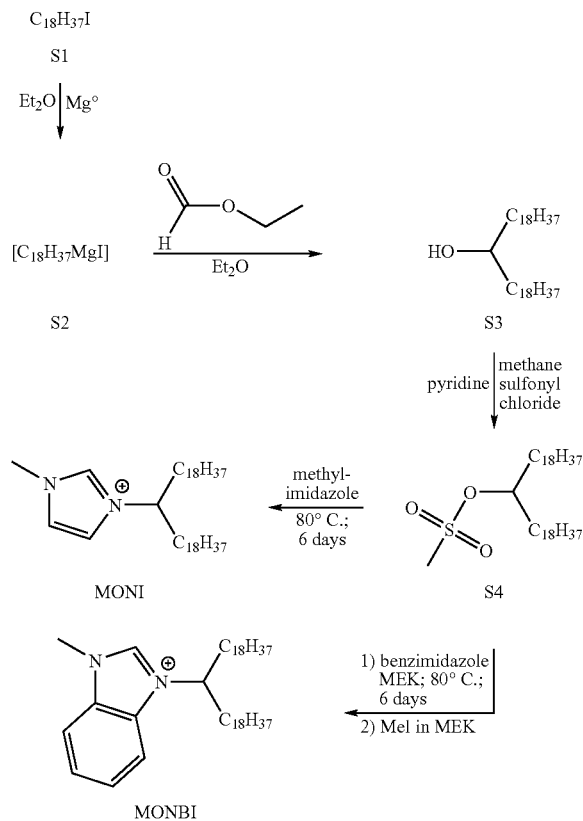

Example 3

Synthesis of HEIC

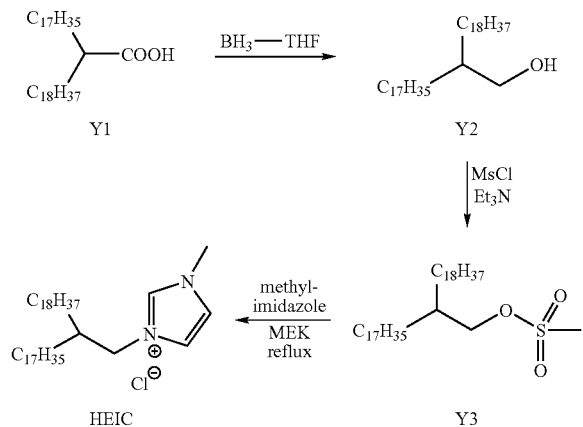

Synthesis of 2-Heptadecyl-eicosanoic acid (Y1)

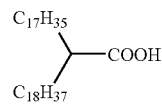

$C_{37}H_{74}O_2$; MW=550.98

Diisopropylamine (2.56 ml; 1.85 g; 18.26 mmoles; MW=101.19) is introduced in a 100 ml oven-dried reaction vessel containing 15 ml THF (distilled over sodium-benzophenone) and cooled to −78° C. under an argon atmosphere. 11.4 ml butyl-lithium (1.6 M in THF; 18.26 mmoles) are added drop-wise, stirred for 10 minutes at −78° C. and warmed up to 0° C., for completion of the formation of the LDA reagent.

Nonadecanoic acid (2.5 g; 8.37 mmoles; MW=298.51), dissolved in 20 ml THF, is introduced drop-wise to the reaction mixture at 0° C. 1.2 ml dry DMPU is added (1.246 g; 9.72 mmoles; MW=128.18) and warmed to room temperature to allow formation of dianion intermediate.

A selective C-alkylation is achieved by addition of 1-iodooctodecane (3.15 g; 8.28 mmoles; MW=380.4) at −5° C. Reaction is continued at room temperature for 18 hours.

Work-Up

The reaction mixture is poured onto 100 ml ice-cooled water and acidified by addition of 4 ml concentrated hydrochloric acid. The solvent THF is evaporated under reduced pressure; the mixture is extracted with ethyl acetate and dried over $Na_2SO_4$ (anhydrous). The organic phase is condensed under reduced pressure, the resulting solid being re-crystallized in acetone to give a white powder (4.271 g; 7.75 mmoles, used without further purification in the next step).

Analysis of Carboxylic Acid Y1:

TLC Analysis:

Rf=0.5; solvent: 20% ethyl acetate in heptane; detection: vanilline/sulfuric acid (Merck TLC plates silica gel 60 F254).

$^1$H-NMR (CDCl$_3$) δ (ppm):

0.90 (J=6.8 Hz, triplet, 6H, terminal CH$_3$ of hydrocarbon chains); 1.27 (large multiplet, 62H, CH$_2$ in hydrocarbon chains); 1.50 (large multiplet, 2H, CH$_2$ at beta position from acid); 1.63 (large multiplet, 2H, CH$_2$ at beta' position from acid); 2.38 (multiplet, 1H, CH at alpha position from acid).

Synthesis of 2-Heptadecyl-eicosan-1-ol (Y2)

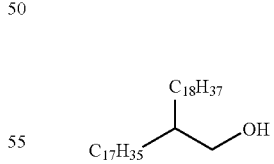

$C_{37}H_{76}O$; MW=537.00

Acid Y1 (847 mg; 1.537 mmoles; MW=550.98) is dissolved in 20 ml dry THF (distilled over sodium benzophenone). A solution of BH$_3$ in THF is added drop-wise at 0° C. (1M in THF; 10 ml; 10 mmoles). The reaction is screened by TLC analysis (solvent: 10% ethyl acetate in heptane). The reaction proceeds smoothly for 2 days. The reaction mixture is poured into 100 ml methanol to precipitate alcohol (1.135 g crude). Silica gel chromatography (gradient: ethyl acetate in heptane: 6% to 10%) yields 518 g of pure Y2 (62%).

Analysis of Alcohol Y2:

TLC:

Rf=0.4; solvent: 10% ethyl acetate in heptane; detection by vanilline/sulfuric acid (blue colour) (Merck TLC plates silica gel 60 F254).

$^1$H-NMR (CDCl$_3$) δ (ppm):

0.90 (J=6.8 Hz triplet, 6H, terminal CH$_3$ from hydrocarbon chains); 1.27 (large multiplet, 66H, CH$_2$ of hydrocarbon chains); 1.46 (large multiplet, 1H, CH beta position from alcohol); 3.56 (J=5.5 Hz, doublet, 2H, CH$_2$ at alpha position from alcohol).

Synthesis of methanesulfonic acid 2-heptadecyl ester (Y3)

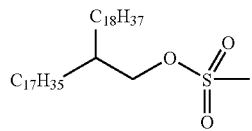

C$_{38}$H$_{78}$O$_3$S; MW=615.09

Alcohol Y2 (600 mg; 1.11 mmole; MW=537.0), dissolved in 10 ml CH$_2$Cl$_2$ (distilled over CaH$_2$), is cooled to 0° C. Mesyl chloride (0.5 ml; 740 mg; 6.46 mmoles; MW=114.55) is introduced into the reaction mixture and 1 ml triethylamine (728 mg; 7.19 mmoles; MW=101.19) is added drop-wise at 0° C. and stirred at room temperature. The reaction is complete after 2 hours by TLC analysis. The reaction mixture is condensed under reduced pressure, and the solid washed with methanol to remove excess reagent. The solid obtained by filtration is pure by NMR analysis and corresponds to 570.6 mg Y3 (0.928 mmoles; 82.9% yield).

Analysis of Mesylate Y3:

TLC:

Rf=0.6; solvent: 50% dichloromethane in heptane; detection by vanilline/sulfuric acid (dark blue spot) (Merck TLC plates silica gel 60 F254).

NMR $^1$H (CDCl$_3$) δ (ppm):

0.90 (J=6.8 Hz, triplet, 6H, terminal CH$_3$ of hydrocarbon chains); 1.27 (large multiplet, 66H, CH$_2$ in hydrocarbon chains); 1.72 (multiplet, 1H, CH at beta position from mesylate); 3.01 (singulet, 3H, CH$_3$ of mesylate); 4.10 (J=5.5 Hz, doublet, 2H, CH$_2$ at alpha position from mesylate).

Synthesis of 1-(2-Heptadecyl-eicosyl)-3-methyl-3H-imidazol-1-ium chloride (HEIC)

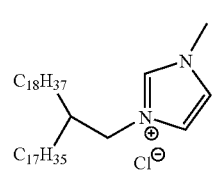

C$_{41}$H$_{81}$ClN$_2$; MW=637.55

Mesylate Y3 (150 mg; 0.243 mmole; MW=615.09) and N-methylimidazole (200 mg; 2.43 mmoles; MW=82.10) are heated in 2-butanone (10 ml) for 5 days at 80° C. TLC analysis allows to screen the conversion of mesylate.

Work-Up

The solvents from the reaction mixture are removed under reduced pressure. The resulting crude product is dissolved in 12 ml isopropanol, filtered through paper to remove un-reacted mesylate and diluted with 8 ml pure water. The mixture is acidified with chlorohydric acid to pH=2. The amphiphilic molecule precipitates at 5° C. as a chlorhydrate salt. The precipitation of HEIC molecule is largely facilitated by the use of isopropanol-water mixtures, being acidified, then by using methanol-water mixtures as described for the other amphiphilic molecules of interest. The product is obtained by centrifugation at 14000 rpm (15 minutes at 0° C.). The resulting precipitate is purified by silica gel column chromatography (methanol gradient in dichloromethane), and 66 mg of pure HEIC are obtained, corresponding to 0.103 mmoles (yield: 42%).

Analysis of Amphiphilic Molecule HEIC:

TLC:

Rf=0.25; solvent: 10% methanol in dichloromethane; detection by iodine vapor (Merck TLC plates silica gel 60 F254).

$^1$H-NMR (CDCl$_3$) δ (ppm):

0.89 (J=6.8 Hz, triplet, 6H, terminal CH$_3$ of hydrocarbon chains); 1.27 (large multiplet, 66H, CH$_2$ in hydrocarbon chains); 1.88 (multiplet, 1H, CH at beta position from imidazolium); 4.16 (singulet, 3H, CH$_3$ of methylimidazolium); 4.20 (J=7.2 Hz, doublet, 2H, CH$_2$ at alpha position from methylimidazolium); 7.14 (singulet, 1H, CH in methylimidazolium); 7.34 (singulet, 1H, CH in methylimidazolium); 10.74 (singulet, 1H, CH in methylimidazolium).

$^{13}$C-NMR: dept 135 (CDCl$_3$) δ (ppm):

CH and CH$_3$ give negative peaks (−)

CH$_2$ detected as positive peaks (+)

Quaternary carbons are not detected by dept135

139.2 ((−), C of methylimidazolium); 122.9 ((−), C of methylimidazolium); 121.5 ((−), C of methylimidazolium); 54.04 ((+), C at alpha position from imidazolium)); 38.8 ((−), methyl-C of methylimidazolium); 36.8 ((−), C at beta position from imidazolium); 31.9 (+); 30.8 (+); 29.7 (+); 29.2 (+); 26.2 (+); 22.7 (+) (different Cs in the hydrocarbon chain); 14.1 (−), C terminal methyls of hydrocarbon chains.

Example 4

Synthesis of HEMB

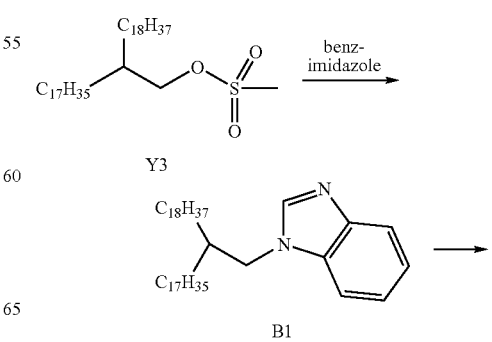

-continued

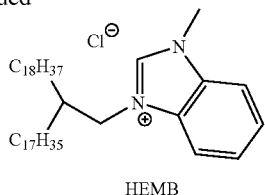

HEMB

Synthesis of
1-(2-Heptadecyl-eicosyl)-1H-benzoimidazole (B1)

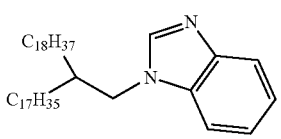

$C_{44}H_{80}ClN_2$; MW=637.12

Mesylate Y3 (150 mg; 0.243 mmole; MW=615.09), dissolved in 10 ml 2-butanone, is heated in presence of 287 mg benzimidazole (2.43 mmoles; MW=118.14) at 80° C. for 23 days. The coupling reaction is screened by TLC analysis, detecting the slow conversion of mesylate Y3.

The crude solid, obtained after evaporation of solvents under reduced pressure, is purified by column chromatography on silica gel (methanol gradient in dichloromethane: 1 to 4%). UV positive fractions give the pure compound B1 in 31 mg quantity (0.048 mmole; 20% yield).

Analysis of Benzimidazole Compound B1:

TLC:

Rf=0.65; solvent: 5% methanol in dichloromethane; UV detection and/or iodine vapors (Merck TLC plates silica gel 60 F254).

$^1$H-NMR (CDCl$_3$) δ (ppm):

0.90 (J=6.8 Hz, triplet, 6H, terminal CH$_3$ of both hydrocarbon chains); 1.25 (large multiplet, 66H, CH$_2$ in hydrocarbon chains); 1.89 (multiplet, 1H, CH at beta position from benzimidazole); 4.1 (J=7.2 Hz, doublet, 2H, CH$_2$ at alpha position from benzimidazole); 7.32 (multiplet, 2H, CH=CH in aromatic ring system); 7.41 (multiplet, 1H, CH in aromatic ring system); 7.84 (multiplet, 1H, CH in aromatic ring system); 7.93 (singulet, 1H, CH in benzimidazole ring).

Synthesis of 3-(2-Heptadecyl-eicosyl)-1-methyl-3H-benzoimidazol-1-ium chloride (HEMB)

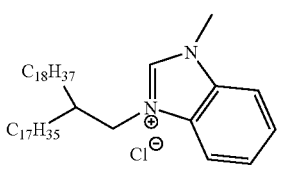

$C_{45}H_{83}ClN_2$; MW=687.61

Iodomethane (0.5 ml; 7.85 mmoles; MW=141.94) is added to: B1 (19.1 mg; 0.0299 mmole, MW=637.12), dissolved in 15 ml 2-butanone, and heated at 60° C. for 24 hours. After evaporation of solvents under reduced pressure 24.1 mg of crude product are obtained. For conversion into the chlorine salt the solid is dissolved in 2.8 ml methanol and acidified with 1.2 ml HCl (18%). The chlorine salt form precipitates at 5° C., and is isolated by centrifugation (14000 rpm, 20 minutes). The residue is further purified by column chromatography on silica gel by a methanol gradient in dichloromethane, yielding 17.7 mg of pure product HEMB (0.0257 mmoles; 86% yield).

Analysis of Amphiphilic Molecule HEMB:

TLC:

Rf=0.2; solvent: 10% methanol in CH$_2$Cl$_2$; UV detection and/or iodine vapors (Merck TLC plates silica gel 60 F254).

$^1$H-NMR (CDCl$_3$) δ (ppm):

0.90 (J=6.8 Hz, triplet, 6H, terminal CH$_3$ of hydrocarbon chains); 1.26 (large multiplet, 66H, CH$_2$ in hydrocarbon chains); 2.14 (multiplet, 1H, CH at beta position from methyl-benzimidazolium); 4.35 (singulet, 3H, CH$_3$ methyl group of methyl-benzimidazolium); 4.49 (J=7.2 Hz, doublet, 2H, CH$_2$ at alpha position from methyl-benzimidazolium); 7.73 (multiplets, 4H, CH=CH of benzyle part); 11.43 (singulet, 1H, CH in imidazolium part).

$^{13}$C-RMN: dept 135 (CDCl$_3$) δ (ppm)

CH and CH$_3$ show up as negative peaks (−).

CH$_2$ give positive peaks (+).

Dept 135 does not show quaternary atoms.

127.1 ((−), 2C in benzo part); 112.8 ((−), C in benzo part); 113.0 ((−), C in benzo part); 51.9 ((+), C at alpha position from methylimidazolium part); 38.1 ((−), CH$_3$ in methylimidazolium part); 33.7 ((−), C at beta from methylimidazolium); 31.9 (+); 31.2 (+); 29.7 (+); 26.3 (+); 22.7 (+): C of hydrocarbon chains; 14.1 ((−), terminal methyl of hydrocarbon chains)

Example 5

Synthesis of HET

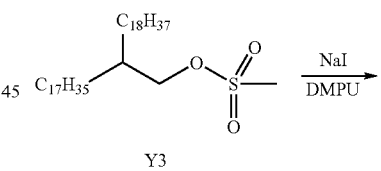

Y3

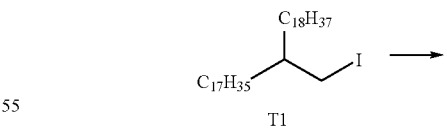

T1

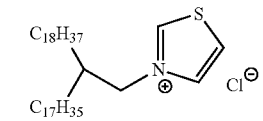

HET

Synthesis of 18-iodomethyl-hexatriacontane (T1)

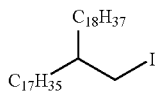

$C_{37}H_{75}I$; MW=646.90

Mesylate Y3 (560.6 mg; 0.911 mmole; MW=615.09), dissolved in 15 ml dry DMPU, is heated together with 682.5 mg sodium iodide (4.55 mmoles, MW=149.85) at 70° C. for 20 hours.

The reaction mixture is diluted with 10 ml water and extracted 3 times with diethylether. The organic phase is dried over $MgSO_4$, filtered off, and the solvents removed under reduced pressure. The resulting solid is purified by column chromatography on silica gel with heptane to give 360.5 mg of pure T1 (0.557 mmole; 61.1% yield).

Analysis of Iodoalcane T1:

TLC:

Rf=0.95; solvent: heptane; detection by vanilline/sulfuric acid (blue spots) (Merck TLC plates silica gel 60 F254).

$^1$H-NMR (CDCl$_3$) δ(ppm):

0.90 (J=6.8 Hz, triplet, 6H, terminal $CH_3$ of both chains); 1.28 (large multiplet, 66H, $CH_2$ in hydrocarbon chains); 2.01 (multiplet, 1H, CH at beta position from iodo); 3.28 (J=4.5 Hz, doublet, 2H, $CH_2$ at alpha position from iodo).

Synthesis of 3-(2-Heptadecyl-eicosyl)-thiazol-3-ium chloride (HET)

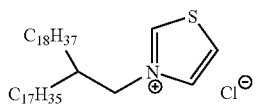

$C_{40}H_{78}ClNS$; MW=640.57

Thiazole (180 mg; 2.11 mmoles; MW=85.13) is added to a solution of T1 (136.9 mg; 0.211 mmole, MW=646.9) in 10 ml 2-butanone, and the reaction mixture is heated at 80° C. for 27 days. The solvents are evaporated under reduced pressure, and the crude solid is dissolved in methanol; un-reacted iodoalcane is filtered off. Diluted chlorhydric acid is added to the methanolic solution (5 ml 4% HCl to 10 ml MeOH solution) and placed at 5° C. to precipitate the amphiphilic molecule, collected by centrifugation at 14000 rpm (30 minutes). The crude product is further purified by silica gel column chromatography with a methanol gradient in dichloromethane. The positive fractions give 21 mg of pure HET (0.033 mmoles; 15% yield).

Analysis of Amphiphilic Molecule HET:

TLC:

Rf=0.4; solvent: 10% methanol in dichloromethane; detection by iodine vapors (Merck TLC plates silica gel 60 F254).

$^1$H-NMR (CDCl$_3$) δ (ppm):

0.89 (J=6.7 Hz, triplet, 6H, terminal $CH_3$ of hydrocarbon chains); 1.27 (large multiplet, 66H, $CH_2$ in hydrocarbon chains); 2.03 (multiplet, 1H, CH at beta position from thiazolium); 4.67 (J=7.4 Hz, doublet, 2H, $CH_2$ at alpha position from thiazolium); 8.22 (J=1.2 Hz, J'=3.7 Hz, doublet of doublets, 1H, CH in thiazolium ring); 8.40 (J'=3.7 Hz, J''=2.5 Hz, doublet of doublets, 1H, $CH_c$ in thiazolium ring); 10.82 (small doublet of doublets, 1H, CH in thiazolium ring).

$^{13}$C-NMR: dept 135 (CDCl$_3$) δ (ppm):

CH and $CH_3$ show up as negative peaks (−).

$CH_2$ give positive peaks (+).

160 ((−), C in thiazolium ring); 136.7 ((−), C in thiazolium); 127.3 ((−), C in thiazolium); 60.7 ((+), C at alpha position from thiazolium); 39.4 ((−), C at beta position from thiazolium); 32.2 (+), 30.7 (+), 29.8 (+), 29.7 (+), 29.7 (+), 29.6 (+), 29.5 (+), 29.4 (+), 26.1 (+), 22.7 (+), C in hydrocarbon chain; 14.1 ((−), C terminal methyl in hydrocarbon chains).

Example 6

Synthesis of HEMI

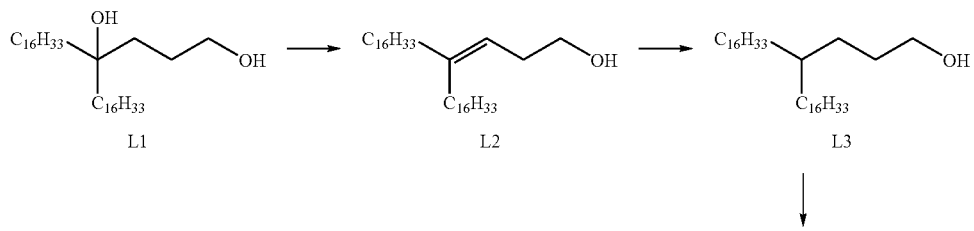

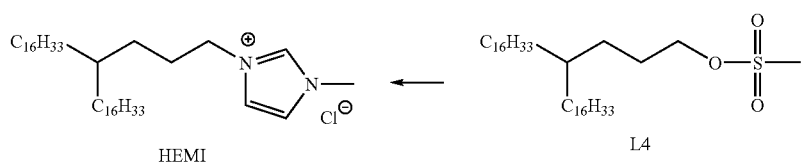

Synthesis of 4-hexadecyl-eicosane-1,4-diol (L1)

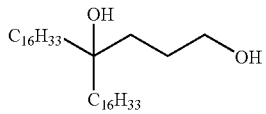

$C_{36}H_{74}O_2$; MW=538.97

Metallic magnesium turnings (1.618 g; 66.6 mmoles; MW=24.31) are introduced in an oven-dried two-necked reaction vessel topped with a refrigeration column and placed under an argon atmosphere. Iodohexadecane (19.55 g; 55.48 mmoles; MW=352.34) dissolved in 10 ml dry diethyl ether is added drop-wise to the magnesium turnings while heating to reflux during 30 minutes. The reaction mixture is heated for additional 60 minutes, and turns to grayish color showing formation of the Grignard reagent.

Butyrolactone (800 mg; 9.29 mmoles; MW=86.09), dissolved in 5 ml dry diethyl ether, is added drop-wise at 0° C. to the organomagnesium reagent. The reaction is warmed up to room temperature and stirred for 18 hours.

Work Up

The reaction mixture is poured onto 200 g split ice, and the aqueous phase is acidified by adding concentrated chlorohydric acid. The resulting mixture is extracted with $CH_2Cl_2$, and the organic phase washed again with pure water. The organic layer is condensed under reduced pressure and dried. The resulting solid is dissolved in warm THF. An insoluble by-product precipitates when cooling the concentrated mixture. After evaporation of THF, the resulting solid is re-crystallized in warm acetone. The diol selectively precipitates. 4.357 g pure diol L1 are obtained corresponding to 87% yield based on butyrolactone.

Analysis of Diol L1:

TLC:

Rf=0.35; solvent: 30% ethyl acetate in heptane; detection with vanilline/sulfuric acid (Merck TLC plates silica gel 60 F254).

$^1$H-NMR (CDCl$_3$) δ (ppm):

0.90 (J=6.8 Hz, triplet, 6H, terminal CH$_3$ of hydrocarbon chains); 1.27 (large multiplet, 56H, CH$_2$ in hydrocarbon chains); 1.45 (large multiplet, 4H, CH$_2$ at beta position from tertiary alcohol); 1.55 (multiplet, 2H, CH$_2$ at gamma position from primary alcohol); 1.66 (multiplet, 2H, CH$_2$ at beta position from primary alcohol); 3.68 (J=6 Hz, triplet, 2H, CH$_2$ at alpha position from primary alcohol).

Synthesis of 4-hexadecyl-eicos-3-en-1-ol (L2)

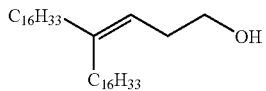

$C_{36}H_{72}O$; MW=520.96

Alcohol L1 (1.5 g; 2.78 mmoles; MW=538.97), dissolved in 100 ml xylene, is heated in presence of 50 mg para-toluenesulfonic acid (0.29 mmole; MW=172) at 130° C. for 50 minutes. The purification of alcenols by silica gel chromatography with a 10% mixture of ethyl acetate in heptane gives 202.4 mg alcenols L2, corresponding to 0.389 mmoles (14% yield) of isomers. The major by-product is 5-membered cyclic ether (1.177 g, 2.2 mmoles, 79%).

Analysis of Alcenols L2:

TLC:

Rf=0.52 and 0.54 (2 spots for different isomers); solvent: 20% ethyl acetate in heptane; detection with vanilline/sulfuric acid (Merck TLC plates silica gel 60 F254).

Synthesis of 4-hexadecyl-eicosan-1-ol (L3)

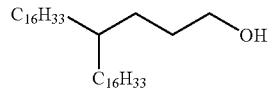

$C_{36}H_{74}O$; MW=522.97

The alcenols L2 (202.4 mg, 0.389 mmole, MW=520.96), dissolved in 5 ml ethyl acetate, are hydrogenated with 60 mg palladium on charcoal (10% Pd/C) under 1 atmosphere pressure of hydrogen during 3 days. The conversion is screened by TLC analysis. The catalyst is removed by filtration, and pure alcohol L3 is obtained by evaporation of solvents' in quantitative yield.

Analysis of Alcohol L3:

TLC:

Rf=0.52; solvent: 20% ethyl acetate in heptane; detection with vanilline/sulfuric acid (Merck TLC plates silica gel 60 F254).

$^1$H-RMN (CDCl$_3$) δ (ppm):

0.90 (J=6.8 Hz, triplet, 6H, terminal CH$_3$ of hydrocarbon chains); 1.27 (large multiplet, 63H, in hydrocarbon chains); 1.56 (multiplet, 2H, CH$_2$ at beta position from alcohol); 3.68 (J=6.7 Hz, triplet, 2H, CH$_2$ at alpha position from alcohol functionality).

Synthesis of methanesulfonic acid 4-hexadecyl-eicosyl ester (L4)

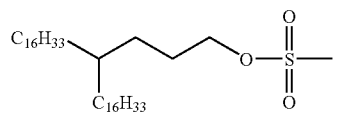

$C_{37}H_{76}O_3S$; MW=601.06

The alcohol L3 (165.2 mg; 0.316 mmole; MW=522), dissolved in 10 ml dichloromethane (distilled over calcium hydride) and cooled to 0° C., is mesylated by successive additions of 0.24 ml mesyl chloride (355 mg; 3.1 mmoles; MW=114.55) and 0.48 ml triethylamine (346 mg; 3.42 mmoles; MW=101.19). After 4 hours at room temperature, the solvents are evaporated, and the solid is washed with methanol to extract excess reagent and triethylamine salts to give 119 mg L4 (0.198 mmoles; 63.6% yield).

Analysis of Mesylate L4:

TLC:

Rf=0.6; solvent: 50% CH$_2$Cl$_2$ in heptane; detection with vanilline/sulfuric acid (Merck TLC plates silica gel 60 F254).

$^1$H-NMR (CDCl$_3$) δ (ppm):

0.90 (J=6.8 Hz, triplet, 6H, terminal CH$_3$ of hydrocarbon chains); 1.27 (large multiplet, 63H, in hydrocarbon chains); 1.73 (multiplet, 2H, CH$_2$ at beta position from mesylate); 3.02

(singulet, 3H, CH₃ of mesylate); 4.22 (J=6.6 Hz, triplet, 2H, CH₂ at alpha position from mesylate).

Synthesis of 1-(4-hexadecyl-eicosyl)-3-methyl-3H-imidazol-1-ium chloride (HEMI)

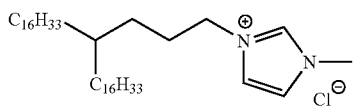

$C_{40}H_{79}N_2Cl$; MW=623.52

Mesylate L4 (119 mg; 0.197 mmol; MW=601.06), dissolved in 10 ml 2-butanone, is heated in presence of 162.5 mg methylimidazole (1.98 mmoles; MW=82.10) at 80° C. for 6 days. Reaction is screened by TLC analysis (disappearance of mesylate).

Work-Up

Evaporation of solvents under reduced pressure. The product is dissolved in methanol, and separated from un-reacted mesylate by filtration. The soluble part is dissolved in 17 ml methanol, and 8 ml 3.7% chlorohydric acid are added. The amphiphilic molecule precipitates upon storage at 5° C. The solid is isolated by centrifugation at 14000 rpm at 0° C., which precipitates 170.6 mg of crude product. Purification by silica gel chromatography (methanol gradient in dichloromethane: 1% to 15%) gives the pure product in 43% yield (53 mg; 0.085 mmoles).

Analysis of Amphiphilic Molecule HEMI:

TLC:

Rf=0.28; solvent: 10% methanol in CH₂Cl₂; detection with iodine vapors (Merck TLC plates silica gel 60 F254).

¹H-NMR (CDCl₃) δ (ppm):

0.87 (J=6.8 Hz, triplet, 6H, terminal CH₃ of hydrocarbon chains); 1.23 (large multiplet, 63H, in hydrocarbon chains); 1.85 (multiplet, 2H, CH₂ at beta position from methylimidazolium); 4.12 (singulet, 3H, CH₃ of methylimidazolium); 4.27 (J=7.4 Hz, triplet, 2H, CH₂ at alpha position from methylimidazolium); 7.28 (singulet, 1H, CH in methylimidazolium ring); 7.49 (singulet, 1H, CH in methylimidazolium ring); 10.65 (singulet, 1H, CH in methylimidazolium ring).

¹³C-NMR: dept 135 (MeOD-4-d) δ (ppm):

CH and CH₃ give negative peaks (−).

CH₂ detected as positive peaks (+).

Quaternary carbons are not detected by dept135.

136.5 ((−), C of methylimidazolium); 123.6 ((−), C of methylimidazolium); 122.3 ((−), C of methylimidazolium); 49.8 ((+), C at alpha position from imidazolium)); 36.9 ((−), methyl-C of methylimidazolium); 35.1 ((−), C at branching point of lateral chain); 33.0 (+); 31.7 (+); 30.0 (+); 29.7 (+); 29.4 (+); 29.35 (+); 29.3 (+); 29.1 (+); 27.2 (+); 26.2 (+); 22.4 (+) (different Cs in the hydrocarbon chain); 13.2 (−), C terminal methyl of hydrocarbon chains.

Example 7

Synthesis of BIA

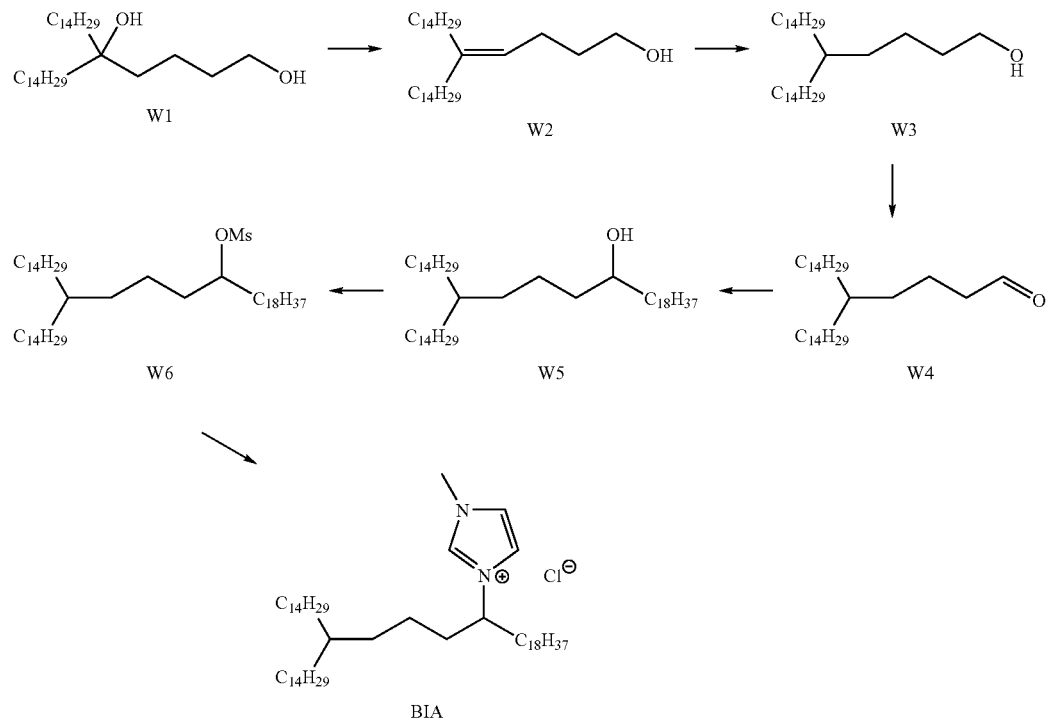

Synthesis of 5-tetradecyl-nonadecyl-1,5-diol (W1)

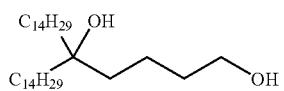

$C_{33}H_{68}O_2$; MW=496.89

1-Bromotetradecane (44.58 g; 160.8 mmoles; MW=277.28), dissolved in 120 ml diethylether (distilled over sodium-benzophenone), is added drop-wise to 4.7 g magnesium turnings (193.3 mmoles; MW=24.31) during 30 minutes, while heating to reflux. Reflux is maintained for 1 hour, then temperature is lowered to 5° C., and valerolactone (4.024 g; 40.2 mmoles; MW=100.12), dissolved in 20 ml diethylether, is added drop-wise. To complete the reaction, the reaction mixture is stirred at room temperature for 16 hours.

Work-Up

The reaction mixture is poured onto 500 ml split ice, acidified with concentrated chlorohydric acid and extracted with dichloromethane. The solid obtained after evaporation of the organic layer is dissolved in warm THF, which allows separation from an insoluble by-product. The soluble component, after evaporation of THF, is re-crystallized in warm acetone, yielding 17.6 g pure diol W1 (35.4 mmoles; 88.1% based on valerolactone).

Analysis of Diols W1:

TLC:

Rf=0.27; solvent: 30% ethyl acetate in heptane; detection with vanilline/sulfuric acid (Merck TLC plates silica gel 60 F254).

$^1$H-NMR (CDCl$_3$) δ (ppm):

0.90 (J=6.8 Hz, triplet, 6H, terminal CH$_3$ of hydrocarbon chains); 1.27 (large multiplet, 50H, CH$_2$ in hydrocarbon chains); 1.42 (large multiplet, 6H, CH$_2$ at beta position from tertiary alcohol); 1.59 (multiplet, 2H, CH$_2$ at beta position from primary alcohol); 3.68 (J=6.4 Hz, J=5.3 Hz, doublet of triplets, 2H, CH$_2$ at alpha position from primary alcohol).

Formation of 5-tetradecyl-nonadec-4-en-1-ol (W2)

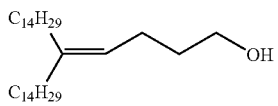

C$_{33}$H$_{66}$O; MW=478.88

Diol W1 (5 g; 10.1 mmole; MW=497), dissolved in 200 ml toluene, is heated at reflux with 137.6 mg para-toluene sulfonic acid for 2.5 hours. The crude solid, obtained after evaporation of solvents under reduced pressure, is purified by silica gel chromatography with an ethyl acetate gradient in heptane (5% to 10%).

2.25 g of alcenols W2 (mixture of isomers) are obtained in pure form (47.1 mmoles; 46.5% yield).

Analysis of Alcenols W2:

TLC:

Rf=0.44; Rf'=0.48; solvent: 20% ethyl acetate in heptane; detection with vanilline/sulfuric acid (Merck TLC plates silica gel 60 F254).

$^1$H-NMR (CDCl$_3$) δ (ppm):

0.90 (J=6.8 Hz, triplet, 6H, terminal CH$_3$ of hydrocarbon chains); 1.28 (large multiplet, 48H, CH$_2$ in hydrocarbon chains); 1.4-1.6 (large multiplet, 2H, CH$_2$ at beta positions from alcohol); 2.00 (multiplet, 6H, CH$_2$ at allylic positions); 3.66 (J=6.4 Hz, triplet, 2H, CH$_2$ at alpha position from primary alcohol); 5.13 (J=7.0 Hz, triplet, 1H, CH at vinylic position).

Formation of 5-tetradecyl-nonadecan-1-ol (W3)

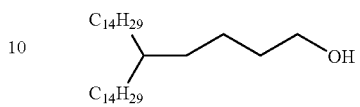

C$_{33}$H$_{68}$O; MW=480.89

Mixture of alcenol isomers W2 (2.207 g, 4.6 mmole), dissolved in 12 ml ethyl acetate, is hydrogenated with Palladium on charcoal (Pd/C 10%, 400 mg) for 24 hours at 1 atmosphere pressure of hydrogen.

The pure alcohol is obtained after filtration over paper and evaporation of solvents under reduced pressure in quantitative yield (2.045 g, 4.25 mmoles, 92.4% yield).

Analysis of Alcohol W3:

TLC:

Rf=0.38; solvent: 20% ethyl acetate in heptane; detection with vanilline/sulfuric acid (Merck TLC plates silica gel 60 F254).

$^1$H-RMN (CDCl$_3$) δ (ppm):

0.90 (J=6.8 Hz, triplet, 6H, terminal CH$_3$ of hydrocarbon chains); 1.28 (large multiplet, 57H, in hydrocarbon chains); 1.56 (multiplet, 2H, CH$_2$ at beta position from alcohol); 3.67 (J=6.6 Hz, triplet, 2H, CH$_2$ at alpha position from alcohol functionality).

Formation of 5-tetradecyl-nonadecanal (W4)

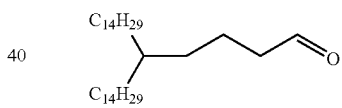

C$_{33}$H$_{66}$O; MW=478.88

The Swern reagent is prepared by successive addition of 284 mg oxalyl chloride and 265 µl DMSO in 20 ml dry dichloromethane previously cooled to −78° C. The alcohol W3 (900 mg; 1.869 mmoles; MW=480.88) is added after 5 minutes and kept at −78° C. for 30 minutes; 1 ml dry triethylamine (distilled over calcium hydride) is added. The reaction mixture is allowed to warm up to room temperature for 30 minutes.

Work-Up the reaction mixture is quenched with 30 ml water and extracted 3 times with dichloromethane. The organic phase is washed with 1% chlorohydric acid and with a 5% aqueous solution of sodium carbonate. The organic layer is dried over anhydrous sodium sulfate and filtered. The crude aldehyde, obtained after evaporation of solvents, is further purified by silica gel chromatography with a gradient of ethyl acetate in heptane (3% to 5%) to yield 658 mg pure aldehyde (1.375 mmoles, 73.5% yield).

Analysis of Aldehyde (W4):

TLC:

Rf=0.32; solvent: 5% ethyl acetate in heptane; detection with 0.5% KMnO$_4$ in water as spray (Merck TLC plates silica gel 60 F254).

¹H-RMN (CDCl₃) δ (ppm):

0.90 (J=6.8 Hz, triplet, 6H, terminal CH₃ of hydrocarbon chains); 1.28 (large multiplet, 57H, in hydrocarbon chains); 1.62 (multiplet, 2H, CH₂ at beta position from aldehyde); 2.42 (J=7.3 Hz, triplet, 2H, CH₂ at alpha position from aldehyde functionality); 9.79 (singulet, CHO of aldehyde).

Formation of 15-tetradecyl-heptatriacontan-19-ol (W5)

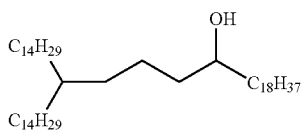

$C_{51}H_{104}O$; MW=733.37

1-iodooctadecane (2.044 g, 5.37 mmoles, MW=380.40), dissolved in 10 ml diethylether (distilled over sodium-benzophenone), is added drop-wise to 196 mg magnesium turnings (8.064 mmoles, MW=24.31) during 20 minutes, while heating to reflux. Reflux is maintained for 1 hour, then temperature is lowered to 5° C., and aldehyde W4 (426 mg; 0.89 mmoles; MW=478.88), dissolved in 20 ml diethylether, is added drop-wise. To complete the reaction, stirring is continued at room temperature for 18 hours.

Work-Up:

the reaction mixture is poured onto 100 ml split ice, acidified with chlorohydric acid and extracted 3 times with dichloromethane. The solid obtained after evaporation of the organic layer is dissolved in warm THF; crystallization allows separation of a by-product that is filtered off. After evaporation of the THF, the crude solid is re-crystallized in warm acetone, and purified by silica gel chromatography with an ethyl acetate heptane gradient (1% to 5%) to yield 293 mg (0.4 mmoles; 45% yield based on aldehyde).

Analysis of Alcohol (W5):

TLC:

Rf=0.37; solvent: 10% ethyl acetate in heptane; detection with vanilline/sulfuric acid (Merck TLC plates silica gel 60 F254).

¹H-NMR (CDCl₃) δ (ppm):

0.90 (J=6.8 Hz, triplet, 9H, terminal CH₃ of hydrocarbon chains); 1.28 (large multiplet, 89H, in hydrocarbon chains); 1.43 (large multiplet, 4H, CH₂ at beta position from secondary alcohol); 3.61 (multiplet, 1H, CH₂ at alpha position from primary alcohol).

Synthesis of methanesulfonic acid 1-octadecyl-5-tetradecyl-nonadecyl ester (W6)

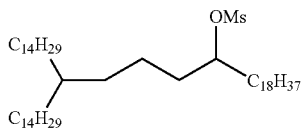

$C_{52}H_{106}O_3S$; MW=811.46

Alcohol W5 (435.8 mg; 0.594 mmole; MW=733.37), dissolved in 20 ml CH₂Cl₂ (distilled over CaH₂), is cooled to 0° C. Mesyl chloride (0.46 ml; 680.7 mg; 6.43 mmoles; MW=114.55) is introduced into the reaction mixture and 0.9 ml triethylamine (661 mg; 6.53 mmoles; MW=101.19) is added drop-wise at 0° C.; the mixture is stirred at room temperature for additional 20 hours. After evaporation of the solvents, the residue is washed with methanol, and separated by filtration to yield pure mesylate (450.5 mg; 0.515 mmoles; 93% yield).

Analysis of Mesylate W6:

TLC:

Rf=0.59; solvent: 50% dichloromethane in heptane; detection with vanilline/sulfuric acid (Merck TLC plates silica gel 60 F254).

¹H-NMR (CDCl₃) δ (ppm):

0.90 (J=5.6 Hz, triplet, 9H, terminal CH₃ of hydrocarbon chains); 1.28 (large multiplet, 89H, in hydrocarbon chains); 1.69 (large multiplet, 4H, CH₂ at beta position from mesylate); 3.01 (singlet, 3H, CH₃ of mesylate); 4.72 (multiplet, 1H, CH at alpha position from mesylate).

Synthesis of <<Branched Imidazolium Amphiphile>> (BIA) (1-methyl-3-(1-octadecyl-5-tetradecyl-nonadecyl)-3H-imidazol-1-ium chloride)

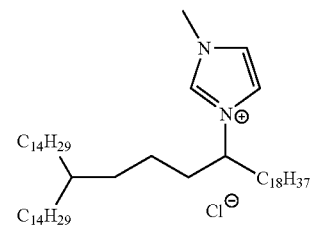

$C_{55}H_{109}ClN_2$; MW=833.92

Mesylate W6 (224 mg; 0.27 mmol; MW=811.46), dissolved in 10 ml 2-butanone, is heated in presence of 221.6 mg methylimidazole (2.7 mmoles; MW=82.10) at 80° C. for 6 days. Reaction is screened by TLC analysis (disappearance of mesylate).

Work-Up

Evaporation of solvents under reduced pressure. The product is dissolved in methanol, and separated from un-reacted mesylate by filtration. The soluble part is dissolved in 17 ml methanol, and 8 ml water are added. The methanolic solution is acidified with concentrated chlorohydric acid to pH=2. The amphiphilic molecule precipitates upon storage at −20° C. The solid is isolated by centrifugation at 14000 rpm at 0° C., which precipitates 220 mg of crude product. Purification by silica gel chromatography (methanol gradient in dichloromethane: 1% to 12%) gives the pure product in 43% yield (198.7 mg; 0.238 mmoles).

Analysis of BIA:

TLC:

Rf=0.33; solvent: 10% methanol in dichloromethane; detection with iodine vapor (Merck TLC plates silica gel 60 F254).

¹H-NMR (CDCl₃) δ (ppm):

0.90 (J=6.8 Hz, triplet, 9H, terminal CH₃ of hydrocarbon chains); 1.28 (large multiplet, 89H, in hydrocarbon chains); 1.84 (large multiplet, 4H, CH₂ at beta position from imidazolium); 4.18 (singulet, 3H, CH₃ of imidazolium); 4.44 (quintuplet, J=5.6 Hz, 1H, CH at alpha position from imidazolium); 7.15 (singulet, 1H, CH in imidazolium ring); 7.33 (singulet, 1H, CH in imidazolium ring); 11.19 (singulet, 1H, CH in imidazolium ring).

$^{13}$C-NMR: dept 135 (CDCl$_3$) δ (ppm):

CH and CH$_3$ give negative peaks (−).

CH$_2$ detected as positive peaks (+).

Quaternary carbons are not detected by dept135.

138.7 ((−), C of methylimidazolium); 123.0 ((−), C of methylimidazolium); 119.3 ((−), C of methylimidazolium); 62.8 ((−), C at alpha position from imidazolium)); 37.2 ((−), CH in hydrocarbon chains), 36.7 ((−), methyl-C of methylimidazolium); 35.9 (+); 35.4 (+); 33.5 (+); 33.4 (+); 33.3 (+); 31.9 (+); 30.1 (+); 29.7 (+); 29.65 (+); 29.6 (+); 29.5 (+); 29.4 (+); 29.1 (+); 26.65 (+); 26.6 (+); 25.9 (+); 23.2 (+); 22.7 (+): (different Cs in the hydrocarbon chain); 14.1 ((−), C terminal methyl of hydrocarbon chains)

Mass Analysis of Amphiphilic Molecules:

|  | Molecular Weight (Da) | Calculated exact mass of cationic part (Da) | Ionic species detected by ESI+ (Da) |
| --- | --- | --- | --- |
| MONI | 637.55 | 601.64 | 601.7 |
| MONBI | 687.61 | 651.66 | 651.7 |
| HEIC | 637.55 | 601.64 | 601.7 |
| HEMB | 687.61 | 651.66 | 651.7 |
| HET | 640.57 | 604.58 | 604.6 |
| HEMI | 623.52 | 587.62 | 587.7 |
| BIA | 833.92 | 797.86 | 797.9 |

Molecules were dissolved in methanol (0.1 mg/ml); direct injection; detection by electrospray ESI+ Mass Analysis on a Bruker HCTultra apparatus.

Preparation of liposomes from 1-methyl-3-(1-octadecyl-nonadecyl)-3H-imidazol-1-ium chloride (MONI) and DOPE Liposomes are formed taking DOPE (dioleoylphosphatidyl ethanolamine) as a co-lipid. 6.3 mg of MONI are dissolved together with different amounts of DOPE in 1 ml of ethanol under soft sonication in a sonication bath. This concentrated alcoholic solution is injected into 9 ml of sterile water. The resulting solution is clear and slightly bluish. This solution is sonicated with an ultrasonic processor (Bioblock Scientific) with 2 second pulses of 11 W during 5 minutes.

The resulting liposomes have a size of about 110 nm with a narrow distribution within their size. They stay stable upon storage at 5° C., without increase of size or precipitation.

In the following formulations of MONI the amphiphile is chosen at a constant concentration of 1 mM taken together with varying millimolar amounts of dioleoylphosphatidylethanolamine (DOPE).

For clarity they are simplified as MONI (1+n), n being the millimolar concentration of DOPE.

The amphiphilic molecule MONI, but also the other amphiphiles of the invention, particularly those of examples 2 to 7 are easily dissolved in ethanol together with the co-lipid DOPE. As with the liposomal formulations, concentrations of 1 mM of amphiphilic molecule in presence of different molar ratios of DOPE were most convenient for comparison of their respective biological activity. These alcoholic solutions performed the same as the liposomal formulations in in vitro transfection experiments.

Measurement of Particle Size By Dynamic Light Scattering:

Liposomal preparations at 1 mmole of amphiphile with varying concentrations of DOPE were prepared in milliQ water, as described above. The particle size of these liposomal preparations was determined by light scattering using a Zetamaster (Malvern Instrument, Orsay, France) with the following specifications: sampling time, 30 s; 3 measurements per sample; medium viscosity, 1.0 cP; refractive index (RI) medium, 1.335; RI particle, 1.47; temperature: 25° C., at 633 nm laser wavelength.

NMR Experiments:

The NMR spectra were recorded on a Bruker 400 MHz spectrometer at Carex SA (Illkirch, France).

Elemental Analysis (C, H, N) and Infrared Spectroscopy:

Elemental analysis and Infrared spectroscopy (Vertex 70 in KBr) were done on final products at the <<Institut Charles Sadron UPR22>> in Strasbourg.

Mass Analysis:

Mass analysis was done by electrospray ionization method (ESI+), on HCTultra instrument (Bruker, France) at the Faculty of Pharmacy in Illkirch (IFR85, ULP, University Louis Pasteur, Strasbourg).

Cell Culture

K562 (human chronic myelogenous leukemia, CCL-243) and THP-1 (human peripheral blood monacytic leukemia, TIB-202) cells were grown in RPMI-1640 (Eurobio) and supplemented with 10% fetal bovine serum (FBS, Perbio), 2 mM glutamax (Eurobio), 100 units/ml penicillin (Eurobio), 100 µg/ml streptomycin (Eurobio). HeLa (human cervix epithelial adenocarcinoma, CC1-2), Caski (human cervix carcinoma), SiHa (human cervix squamous carcinoma, HTB-35), MCF-7 (human breast epithelial adenocarcinoma, HTB-22) cells were grown in MEM (Eurobio) supplemented with 2 mM glutamax, Earle's BSS, 1.5 g/L sodium bicarbonate, 0.1 mM non-essential amino acids, 1.0 mM sodium pyruvate, 100 units/ml penicillin, 100 µg/ml streptomycin, and 10% of FBS. NIH-3T3 (mouse embryonic fibroblast, CRL-1658) cells were grown in DMEM (Eurobio) supplemented with 4 mM L-glutamine, 1.5 g/L sodium bicarbonate, 4.5 g/l glucose, and antibiotics (Peni/Strepto) and 10% of FBS.

A549 (human lung carcinoma, ATCC No CCL-185) cells stably expressing the GL3 luciferase (Photinus pyralis luciferase under the control of SV40 elements) were obtained after stable transfection of pGL3Luc plasmid (Clontech). A549-GL3Luc cells were grown in RPMI-1640 and supplemented with 10% fetal bovine serum, 2 mM glutamax, 100 units/ml penicillin, 100 µg/ml streptomycin and 0.8 µg/ml G418 (Promega). All the cells were maintained at 37° C. in a 5% CO$_2$ humidified atmosphere.

Transfection Experiments

Transfection in 24-Well Tissue Culture Plate

One day before transfection, 2.5×10$^4$ cells were seeded in 24-well tissue culture plate in 1 ml fresh complete medium containing 10% FBS. Before transfection, complexes of siRNA/transfection reagent were prepared. The desired amount of siRNAs was diluted in 100 µl of serum-free medium. The solution was mixed with a Vortex for 10 seconds. Then, 0.5 µl to 3 µl of amphiphilic molecules-based formulations were added to siRNA solution. The final mixture was mixed with a Vortex for 10 seconds, and left for 10 minutes at room temperature. Then, 100 µl of complexes solution were added per well and the plates were incubated at 37° C.

Transfection in 96-Well Tissue Culture Plate

One day before transfection, 1×10$^4$ cells were seeded in 96-well tissue culture plate in 0.15 ml fresh complete medium containing 10% FBS. Before transfection, complexes of siRNA/transfection reagent were prepared. The desired amount of siRNAs was diluted in 20 µl of serum-free medium. The solution was mixed with a Vortex for 10 seconds. Then, 0.5 µl to 3 µl of amphiphilic molecules-based formulations were added to siRNA solution. The final mixture was mixed with a Vortex for 10 seconds, and left for 10 minutes at room temperature. Then, 20 µl of complexes solution was added per well and the plates were incubated at 37° C.

Reverse Transfection in 96-Well Tissue Culture Plate

Complexes of siRNA/transfection reagent were prepared first. The desired amount of siRNAs was diluted in 50 µl of serum-free medium and added per well in a 96-well tissue culture plate. Then, 0.5 µl to 3 µl of amphiphilic molecules-based formulations were added to siRNA solution. The plate was placed on an orbital shaker for 5 minutes at room temperature. Then, $1 \times 10^4$ cells were added per well in 96-well tissue culture plate in 125 µl of fresh complete medium containing 10% FBS and the plate was further incubated at 37° C.

Comparison of Transfection Reagents (in 24-Well Tissue Culture Plate Format)

For HiperFect reagent, the desired amount of siRNA was diluted in 300 µl of serum free medium (for triplicate experiment). Then, 9 µl of transfection reagent was added to the siRNA mixture. The solution was mixed with a vortex, 10 seconds and left for 10 minutes at room temperature. Before the transfection, the complete culture medium was removed and replaced by 0.5 ml of complete medium containing 10% FBS per well. One hundred microliters of transfection solution were added per well.

For SilentFect reagent, the desired amount of siRNA was diluted in 75 µl of serum free medium (for triplicate experiment). SilentFect reagent (2.25 µl) was diluted in 75 µl of serum free medium and the solution was added on the diluted solution of siRNA, then mixed, and left for 20 minutes at room temperature. Before the transfection, the complete culture medium was removed and replaced by 0.5 ml of complete medium containing 10% serum per well. Fifty microliters of transfection solution were added per well. As cytotoxicity was seen, the transfection medium was removed and replaced by 1 ml of complete medium containing 10% serum per well.

For Saint-Red reagent, the desired amount of siRNA was diluted in 75 µl of HBS (for triplicate experiment). Saint-Red reagent (0.42 µl for 1 nM of siRNA) was diluted in 75 µl of HBS and the solution was added on the diluted solution of siRNA, then mixed, and left for 15 minutes at room temperature. Then, 600 µl of serum free medium were added on the transfection solution. Before adding to the cells, the complete culture medium was removed and replaced by 0.5 ml of complete medium containing 10% serum per well, then 250 µl of transfection solution were added per well.

For TransIT-TKO, the reagent (6 µl) was diluted in 150 µl of serum free medium and the solution was mixed and left for 15 minutes at room temperature. Desired amount of siRNA was added on the diluted solution of transfection reagent. The solution was gently mixed and left for 15 minutes at room temperature. Before adding to the cells, the complete culture medium was removed and replaced by 0.25 ml of complete medium containing 10% serum per well. Fifty microliters of transfection solution were added per well. After 24 h incubation, the medium was removed and replaced by 0.5 ml of complete medium containing 10% FBS.

For all transfection protocols, the plates were further incubated at 37° C. for 48 h.

Luciferase and Protein Assay

Luciferase gene expression was measured using a commercial kit (Promega, France). After removing the complete medium, three washings with 1 ml of PBS solution were made. Then, 100 µl of 1× lysis buffer were added per well, and the plate was incubated at room temperature for 30 minutes. The lysates were collected and centrifuged at 14,000 g for 5 minutes. The luciferase assay was assessed with 5 µl of lysate after injection of 100 µl of luciferin solution. The luminescence (RLU) was monitored with an integration over 10 seconds with a luminometer (LB960, Berthold, France). Results are expressed as light units integrated over 10 seconds (RLU), per mg of cell protein using the BCA assay (Pierce, France).

Measurement of mRNA Level

Messager RNA level was determined by the QuantiGene® Branched DNA assay (GenoSpectra) which is performed with whole cell lysates and without target amplification.

After 48 h transfection, cells were washed with 1 mL PBS 1× (Cambrex) and lysed in 0.6 mL of 1× Genospectra lysis buffer for 30 min. at 50° C. Then, the plate was stored at −80° C. for at least 30 min. The lysates were thawed and 2 to 20 µl of lysate were adding to the capture plate. Ten µl of lysis working reagent (for 48 reactions, the lysis working reagent is prepared by adding 25 µl of CE (capture extender), 25 µl of LE (label extender) and 25 µl of BL (blocking probe) and 425 µl of 3× lysis mixture, all compounds are from Genospectra) were adding the plate and the volume was completed to 100 µl with 1× lysis mixture. The plate was covered with a lid and incubated for 16 h at 50° C. The plate was wash 3 times with 300 µl of 1× wash buffer (Genospectra), and 100 µl of Amplifier working solution (0.116 µl of amplifier diluted in 116 µl Amplifier diluent, all from Genospectra) were adding to each well. The plate was incubated for 1 hour at 50° C. After 3 times 1× wash buffer washing, 100 µl of Label Probe Working Reagent (0.116 µl of label probe diluted in 116 µl Amplifier diluent, all from Genospectra) were adding to each well and incubate for 1 hour at 50° C. The plate was then wash 3 times with 1× wash buffer and 100 µl of Substrate Working Reagent (0.348 µl of 10% Lithium Lauryl sulphate in 116 µl of Substrate, all from Genospectra) was added to each well. After 30 minutes incubation, the luminescence was measured in each well with a spectrophotometer (Berthold).

SDS-PAGE and Western Blot Analysis

After transfection, the cells were washed with 1 ml PBS 1× (Cambrex) and each well was trypsinized with 100 µl trypsin/EDTA (Euromedex). 0.5 mL of complete medium with 10% serum, was added to stop the trypsin. The wells per triplicate was pooled, centrifuged and the pellet was washed with 1×PBS. After centrifugation, the pellet was lysed in 100 µl of RIPA buffer (50 mM Tris-HCl pH 7.4, 150 mM NaCl, 1 mM EDTA, 1% Triton x-100, 1% Sodium deoxycholate, 0.1% SDS) during 20 min. at 4° C. The lysate was homogenate with a vortex and centrifuged for 5 min. at 14,000 rpm. Protein content was assessed by the BCA kit (Pierce). 5 µg of protein were subjected to electrophoresis on 10% acrylamide/bis acrylamide gel and transferred to polyvinylidene difluoride membrane (Millipore). Vimentin expression was detected with a Guinea Pig anti-vimentin polyclonal antibody (RDI) diluted at 1/3000. The GAPDH, detected with a mouse anti-GAPDH monoclonal antibody (Ambion), was used to normalize the protein level. The immunoreactive proteins were visualized using horseradish peroxidase-conjugated anti-guinea pig or anti-mouse antibodies and Amplified Opti-4CN Substrate Kit from BioRad using the instruction of the manufacturer.

Immunofluorescence Staining

The culture medium was withdrawn 48 to 72 hours after transfection. Cells were washed with PBS solution containing 1% bovine serum albumin (BSA). Cells were permeabilized and fixed with a methanolic solution (methanol/acetone: 1/1, cooled to −20° C.) for 15 minutes at 4° C. Cells were washed again twice with 1 ml PBS-BSA 1%, then the cells were incubated at 4° C. with 1 ml of PBS containing 1% of goat serum for 15 minutes in order to block unspecific binding sites. Cells were washed again with 1 ml PBS-BSA 1%.

Cells were incubated for 1 hour at 4° C. in presence of 50 µl of PBS and 50 µl of mouse antibody anti-lamin A/C (IgG 1 class, Research Diagnostic Inc, Flanders, N.J.). Cells were washed twice with 1 ml of PBS-BSA1%.

The cells were incubated 1 hour at 4° C. in PBS containing 50 µl of goat antibody anti-mouse-IgG coupled to fluoresceine (Calbiochem, La Jolla, Calif.). Cells were then washed again with 1 ml of PBS-BSA1% and finally 1 ml PBS-BSA1% was added per well. Immunostaining was observed by fluorescence microscopy (ECLIPSE TE2000-S, Nikon).

Results

As a target model of endogenous reporter gene, A549 cells stably expressing the GL3 luciferase were used (*Photinus pyralis* luciferase under the control of SV40 elements). A well defined and conventional siRNA, chemically produced, and sequence-specific GL3Luc siRNA of SEQ ID No 1 and 2 composed of a short dsRNA of 19 nucleotides matching the GL3Luc mRNA and comprising 3'-overhangs of 2 deoxyribonucleotides (dT) was used for the transfection experiments. A formulation of cationic amphiphile MONI at 1 mM and combined with neutral phospholipid DOPE at 1 mM in ethanol was prepared. SiRNA diluted in serum-free medium (100 µl) was then complexed with 2 µl of the formulation of MONI/DOPE (1 mM/1 mM in ethanol). The resulting solution of transfection complexes was added on the cells growing in medium containing serum and cells were finally exposed to siRNA concentration range from 100 to 2000 pM (FIG. 1). The silencing efficiency was determined 48 h post-transfection by measuring the luciferase activity with a standard luminescence assay normalized by the protein content of cell lysates. The luciferase activity (expressed as RLU/mg of protein) was inhibited up to 90% when the transfection was performed with 2000 pM of siRNA. The absence of effect on the luciferase activity when cells were transfected with the unrelated sequence, the GL2Luc siRNA, in the same conditions, confirmed a sequence-specific RNA interference. GL3Luc siRNA added alone on the cells and with the same concentration range (100 to 2000 pM) showed also no inhibition of the luciferase activity (not shown).

A second formulation of cationic amphiphile based on MONBI molecule at 1 mM and combined with DOPE at 2 mM was prepared in ethanol. 2 µl of this formulation were used to form complexes with GL3Luc siRNA (concentration range from 250 pM to 5 nM) in serum-free medium and the resulting solution was added on A549-GL3Luc cells. The silencing efficiency was assessed 48 h post-transfection by measuring the luciferase activity. A significant luciferase inhibition (70%) was already observed with 250 pM of siRNA and reached 90% with 5 nM of siRNA transfected (FIG. 2). When the GL2Luc siRNA, used as unrelated sequence and with the same conditions of transfection, the luciferase level was not affected confirming the selective silencing obtained with the GL3Luc siRNA.

Gene silencing was effective at the picomolar range of siRNA when the transfection was achieved with the formulation MONI/DOPE as shown in the FIG. 2. The luciferase gene silencing was 95% and 80% at 1000 and 100 pM, respectively. 50 and 20% of silencing was still observed when 25 and 10 pM of siRNA were transfected, respectively (FIG. 3).

Formulations based on imidazolium amphiphilic derivatives, such as MONI or MONBI, were prepared by mixing cationic amphiphiles with the neutral phospholipid DOPE in ethanol or in water. For liposomal preparations, amphiphiles were first dissolved with DOPE in ethanol providing a 10× concentrated solution. Then, this solution was injected in 10 volumes of water and mixed immediately. The resulting solution was sonicated with an ultrasonic processor. The particles size of formed liposomes was determined by dynamic light scattering and showed a mean size of 100 nm with a low polydispersity (FIG. 4). This liposomal formulation was stored at 4° C. and found to be stable over the time (several weeks to months) without aggregates formation (1 month as shown by FIG. 4). Many liposomal formulations were prepared and showed a mean size of particles of 100+/−10 nm highlighting the robustness of our method of liposomal preparation.

MONI/DOPE liposomal formulation was compared to the last generation of many commercially available transfection reagents specifically proposed for siRNA delivery into cells (FIG. 5). Transfection conditions were applied according to the manufacturer protocols and are described in the 'Materials and Methods'. SiRNA concentration ranging from 1 pM to 10 nM was used. Saint-Red and TransIT-TKO reagents showed the lowest silencing efficiencies (inferior to 50% at 1 nM). HiperFect and SilentFect reagents showed good silencing efficiencies in the range of 100 pM to 10 nM of siRNA but are totally inefficient for the lowest concentrations of siRNA (10 pM to 1 pM). MONI/DOPE transfection system compared favourably to all others transfection reagents tested and with all siRNA concentrations tested. A significant gene silencing, around 50%, is still observable at 10 pM.

In order to confirm the potency of MONI/DOPE formulations to mediate efficient endogenous gene silencing we targeted the GAPDH gene in various cell lines, including adherent and non-adherent cells. We selected GAPDH siRNAs from the SMARTpool® Technologies (Dharmacon) providing a set of four siRNAs targeting multiples sites on the same mRNA and guaranteed for efficient knockdown. Gene silencing was evaluated at the mRNA level using the QuantiGene® bDNA technology (Genospectra) 48 h post-transfection. GAPDH SMART Pool® reagents added alone on all cells tested (HeLa, Caski, SiHa, MCF-7, K562, and THP-1) were unable to provide efficient knockdown at the mRNA level at concentration ranging form 250 pM to 10 nM. When transfected with the liposomal MONI/DOPE formulation (½ mM), GAPDH SMART Pool® reagents showed highly efficient GAPDH mRNA knockdown superior to 80% for adherent cells (HeLa, Caski, SiHa, and MCF-7) and siRNAs concentration from 250 pM to 10 nM (FIG. 6). As control of selectivity, Lamin A/C siRNA was added and showed no effect on the GAPDH mRNA level. In addition, selective and efficient GAPDH silencing was obtained for non-adherent cells (FIG. 6), K562 and THP-1 cells, when transfection was performed with liposomal MONI/DOPE formulation and at low siRNA concentration (5 to 20 nM). Others endogenous genes were targeted for RNA interference, including vimentin and lamin A/C genes. The silencing efficiency was determined at the protein level by western blot for vimentin gene of murine fibroblast 3T3 cells (FIG. 7) and by immunofluorescence staining for lamin A/C gene of human HeLa cells (FIG. 8). Both experiments showed high silencing efficiency 48 h siRNA post-transfection with the liposomal MONI/DOPE formulation (½ mM) for these two abundant proteins at low siRNA concentration (1-5 nM). Lamin A/C experiment confirmed also that all the cells transfected contained bioactive siRNA abolishing totally the gene expression targeted (FIG. 8).

Transfection protocols were initially developed for effective siRNA delivery in adherent and non-adherent cells growing in 24-well tissue culture plates in presence of medium containing serum. Others cell culture supports were tested, such as 6-well plate, T25 and T75 culture flasks, and showed gene silencing efficiency >80% for siRNA concentrations ranging from 100 pM to 10 nM and transfected with the liposomal MONI/DOPE (½ mM) formulation. The potency of siRNA delivery adapted to HTS conditions was addressed by using a reverse transfection procedure applied in 96-well tissue culture plate. After the optimization procedure, a routinely effective protocol was proposed. SiRNA, diluted in 25 μl of serum free medium, was first added in the well. Then, 1 μl of liposomal MONI/DOPE (½ mM) formulation was added per well. After homogenization, the plate was kept at room temperature for 10 min to allow the transfection complexes formation. The cells diluted in 125 μl of medium containing serum were then added in the well (10,000 cells/well) and the plate was further incubated for 48 h at 37° C. The luciferase gene silencing of A549GL3Luc cells was superior to 80% for siRNA concentration ≧1 nM and selective as showed by the absence of luciferase inhibition when the unrelated GL2Luc siRNA was transfected (FIG. 9). Silencing at the picomolar level of siRNA was also significantly obtained (>50%, FIG. 9). Selective GAPDH silencing in MCF-7 cells following the optimized reverse procedure of siRNA transfection was obtained with efficiencies from 70 to 90% for siRNA concentrations of 100 pM and 5 nM, respectively (FIG. 10).

In Table 2 below, are given results concerning the silencing of luciferase gene (pGL3) by GL3Luc siRNA transfected using formulations based on amphiphilic cationic molecules according to the formula (I).

Formulations composed of amphiphilic cationic molecule/DOPE (1 mM/2 mM in 10% ethanol and water) were used to complex siRNA and transfect A549-GL3Luc cells. Luciferase gene expression was measured after 48 h incubation period. Experiments were made in triplicates and the GL3 luciferase silencing efficiency was calculated from the luciferase level of transfected cells with a control GL2-Luc siRNA and normalized by the content of protein in the cell lysates.

| Amphiphilic molecule | siRNA concentration (nM) | Silencing (%) +/− SD |
|---|---|---|
| MONI | 10 | 95 +/− 3 |
|  | 1 | 92 +/− 4 |
| MONBI | 10 | 94 +/− 10 |
|  | 1 | 93 +/− 11 |
| HEIC | 10 | 83 +/− 2 |
|  | 1 | 73 +/− 6 |
| HEMB | 10 | 88 +/− 4 |
|  | 1 | 76 +/− 9 |
| HET | 10 | 23 +/− 2 |
|  | 1 | 22 +/− 1 |
| HEMI | 10 | 67 +/− 19 |
|  | 1 | 57 +/− 8 |
| BIA | 10 | 75 +/− 14 |
|  | 1 | 59 +/− 6 |
| BIA (without DOPE) | 10 | 87 +/− 4 |
|  | 1 | 68 +/− 5 |

BIBLIOGRAPHIC REFERENCES

Cho, J., and R. R. Rando. 2000. Specific binding of Hoechst 33258 to site 1 thymidylate synthase mRNA. *Nucleic Acids Res.* 28:2158-63.

Dassonneville, L., F. Hamy, P. Colson, C. Houssier, and C. Bailly. 1997. Binding of Hoechst 33258 to the TAR RNA of HIV-1. Recognition of a pyrimidine bulge-dependent structure. *Nucleic Acids Res.* 25:4487-92.

Elbashir, S. M., J. Harborth, W. Lendeckel, A. Yalcin, K. Weber, and T. Tuschl. 2001. Duplexes of 21-nucleotide RNAs mediate RNA interference in cultured mammalian cells. *Nature.* 411:494-8.

Elbashir, S. M., W. Lendeckel, and T. Tuschl. 2001. RNA interference is mediated by 21- and 22-nucleotide RNAs. *Genes Dev.* 15:188-200.

Fire, A. 1999. RNA-triggered gene silencing. *Trends Genet.* 15:358-63.

Hammond, S. M., E. Bernstein, D. Beach, and G. J. Hannon. 2000. An RNA-directed nuclease mediates post-transcriptional gene silencing in Drosophila cells. *Nature.* 404:293-6.

Jepsen, J. S., and J. Wengel. 2004. LNA-antisense rivals siRNA for gene silencing. *Curr Opin Drug Discov Devel.* 7:188-94.

Kim, D. H., M. A. Behlke, S. D. Rose, M. S. Chang, S. Choi, and J. J. Rossi. 2005. Synthetic dsRNA Dicer substrates enhance RNAi potency and efficacy. *Nat Biotechnol.* 23:222-6.

Kurreck, J. 2003. Antisense technologies. Improvement through novel chemical modifications. *Eur J Biochem.* 270:1628-44.

Miller, P. S. 1991. Oligonucleoside methylphosphonates as antisense reagents. *Biotechnology (NY).* 9:358-62.

Parrish, S., J. Fleenor, S. Xu, C. Mello, and A. Fire. 2000. Functional anatomy of a dsRNA trigger: differential requirement for the two trigger strands in RNA interference. *Mol Cell.* 6:1077-87.

Siolas, D., C. Lerner, J. Burchard, W. Ge, P. S. Linsley, P. J. Paddison, G. J. Hannon, and M. A. Cleary. 2005. Synthetic shRNAs as potent RNAi triggers. *Nat Biotechnol.* 23:227-31.

Tuschl, T. 2001. RNA interference and small interfering RNAs. *Chembiochem.* 2:239-45.

Tuschl, T., P. D. Zamore, R. Lehmann, D. P. Bartel, and P. A. Sharp. 1999. Targeted mRNA degradation by double-stranded RNA in vitro. *Genes Dev.* 13:3191-7.

Verma, S., and F. Eckstein. 1998. Modified oligonucleotides: synthesis and strategy for users. *Annu Rev Biochem.* 67:99-134.

Yang, D., H. Lu, and J. W. Erickson. 2000. Evidence that processed small dsRNAs may mediate sequence-specific mRNA degradation during RNAi in Drosophila embryos. *Curr Biol.* 10:1191-200.

Yang, X. L., R. B. Hubbard, M. Lee, Z. F. Tao, H. Sugiyama, and A. H. Wang. 1999. Imidazole-imidazole pair as a minor groove recognition motif for T:G mismatched base pairs. *Nucleic Acids Res.* 27:4183-90.

Yang, X. L., C. Kaenzig, M. Lee, and A. H. Wang. 1999. Binding of AR-1-144, a tri-imidazole DNA minor groove binder, to CCGG sequence analyzed by NMR spectroscopy. *Eur J Biochem.* 263:646-55.

Zamore, P. D., T. Tuschl, P. A. Sharp, and D. P. Bartel. 2000. RNAi: double-stranded RNA directs the ATP-dependent cleavage of mRNA at 21 to 23 nucleotide intervals. *Cell.* 101:25-33.

Zelphati, O., and F. C. Szoka, Jr. 1996. Mechanism of oligonucleotide release from cationic liposomes. *Proc Natl Acad Sci USA.* 93:11493-8.

Zon, G., and T. G. Geiser. 1991. Phosphorothioate oligonucleotides: chemistry, purification, analysis, scale-up and future directions. *Anticancer Drug Des.* 6:539-68.

The invention claimed is:

1. Compositions of transfection comprising an oligonucleotide active for gene silencing and an amphiphilic cationic molecule of formula (I)

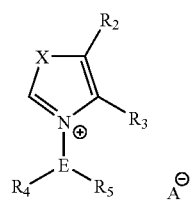

(I) wherein

X is N—$R_1$, $R_1$ being a C1-C4 alkyl radical or an hydroxylated C3-C8 alkyl radical, $R_2$ and $R_3$, identical or different, represent H or a C1-C4 alkyl radical, or $R_2$ and $R_3$ are linked together to form a saturated or unsaturated cycle or a heterocycle having 5 or 6 elements, E is a C1-C5 alkyl spacer, $R_4$ and $R_5$, identical or different, represent saturated or unsaturated, linear or branched, C10-C36 hydrocarbon or fluorocarbon chains, $A^-$ is a biocompatible anion.

2. The compositions of claim 1, wherein said heterocycle formed when $R_2$ and $R_3$ are linked together are unsaturated or saturated and have 5 or 6 elements and comprise C and N, S or O as heteroatoms.

3. The compositions of claim 1, wherein $R_4$ and $R_5$ are C14-C36 hydrocarbon chains and E is a C1-C4 alkyl spacer.

4. The compositions of claim 3, wherein $R_4$ and $R_5$ are identical or different.

5. The compositions of claim 3, wherein $R_4$ and $R_5$ are C18 alkyl radicals and E is a C1 alkyl.

6. The compositions of claim 3, wherein $R_4$ and $R_5$ are C16 alkyl radicals and E is a C4 alkyl.

7. The compositions of claim 3, wherein $R_4$ and $R_5$ are different.

8. The compositions of claim 7, wherein $R_4$ and $R_5$, identical or different, are C18 and C17 alkyl chains, and E is a C2 alkyl.

9. The compositions of claim 7, wherein $R_4$ and $R_5$ are C32 and C18 alkyl radicals, respectively, and E is a C1 alkyl.

10. The compositions of claim 1, wherein $R_2$ and $R_3$ are H or are linked together to form an aromatic cycle.

11. The compositions according to claim 1, wherein X is N—$R_1$, $R_1$ being $CH_3$.

12. The compositions according to claim 1, wherein $A^-$ is $Cl^-$ or OH.

13. The compositions according to claim 1, formulated with a neutral co-lipid.

14. The compositions of claim 13, wherein the co-lipid is a phosphatidylethanolamine derivative.

15. The compositions of claim 1, wherein said oligonucleotide is active for RNA interference.

16. The compositions of claim 15, wherein said oligonucleotide is a siRNA.

17. The compositions of claim 1, wherein said oligonucleotide, comprises groups for their stabilization against degradation, said groups being selected from the group comprising purine nucleotides and pyrimidine nucleotides substituted by modified analogs, and/or modified nucleotide analogs.

18. The compositions according to claim 16, wherein said siRNA contain deoxyribonucleotides, ribonucleotides or nucleotide analogs.

19. Compositions of transfection comprising an oligonucleotide active for gene silencing and an amphiphilic cationic molecule of formula (I)

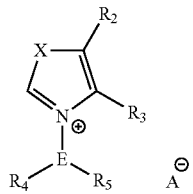

wherein
X is N—$R_1$, $R_1$ a $CH_3$ alkyl radical,
$R_2$ and $R_3$, identical or different, represent H,
E is CH
$R_4$ and $R_5$, identical or different is $C_{19}H_{37}$, and
$A^-$ is a biocompatible anion.

20. The compositions of claim 14, wherein said phosphatidylethanolamine derivate is dioleoylphosphatidylethanolamine (DOPE).

21. The compositions of claim 17, wherein said pyrimidine nucleotides substituted by modified analogs are deoxynucleotides and said modified nucleotide analogs are sugar or backbone modified ribonucleotide or deoxyribonucleotides.

22. The compositions of claim 18, wherein said siRNA contain methylphosphate, morpholino phosphorodiamidate, phosphorothioate, peptide nucleic acid (PNA), locked nucleic acid (LNA) and 2' alkyl nucleotide analogs.

23. The composition according to claim 13, wherein the neutral co-lipid is a cholesterol.

24. The composition according to claim 13, wherein the neutral co-lipid is a lipid-polyethylene glycol conjugate.

* * * * *

UNITED STATES PATENT AND TRADEMARK OFFICE
CERTIFICATE OF CORRECTION

PATENT NO. : 8,399,422 B2  Page 1 of 1
APPLICATION NO. : 12/226027
DATED : March 19, 2013
INVENTOR(S) : Neuberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1115 days.

Signed and Sealed this

First Day of September, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: Desoxythymidine

<400> SEQUENCE: 1
cuuacgcuga guacuucgat t                                               21

<210> SEQ ID NO 2
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (1)..(2)
<223> OTHER INFORMATION: Desoxythymidine

<400> SEQUENCE: 2
ttgaaugcga cucaugaagc u                                               21

<210> SEQ ID NO 3
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: Desoxythymidine

<400> SEQUENCE: 3
cguacgcgga auacuucgat t                                               21

<210> SEQ ID NO 4
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (1)..(2)
<223> OTHER INFORMATION: Desoxythymidine

<400> SEQUENCE: 4
ttgcaugcgc cuuaugaagc u                                               21

<210> SEQ ID NO 5
<211> LENGTH: 20
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (19)..(20)
<223> OTHER INFORMATION: Despxythymidine

```
<400> SEQUENCE: 5
gaaugguaca aauccaagtt                                              20

<210> SEQ ID NO 6
<211> LENGTH: 20
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (1)..(2)
<223> OTHER INFORMATION: Desoxythymidine

<400> SEQUENCE: 6
ttcuuaccau guuuagguuc                                              20

<210> SEQ ID NO 7
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: Desoxythymidine

<400> SEQUENCE: 7
cuggacuucc agaagaacat t                                            21

<210> SEQ ID NO 8
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (1)..(2)
<223> OTHER INFORMATION: Desoxythymidine

<400> SEQUENCE: 8
ttgaccugaa ggucuucuug u                                            21
```